United States Patent [19]

Burcoglu et al.

[11] Patent Number: 5,624,912
[45] Date of Patent: Apr. 29, 1997

[54] METHOD OF TREATING HIV INFECTION AND RELATED SECONDARY INFECTIONS WITH DEFIBROTIDE

[76] Inventors: Arsinur Burcoglu, 213 Sweetgum Rd., Pittsburg, Pa. 15238; Marc Wagner, 4201 Greensburg Pike, Pittsburg, Pa. 15221

[21] Appl. No.: 185,416

[22] Filed: Jan. 24, 1994

Related U.S. Application Data

[63] Continuation-in-part of Ser. No. 748,277, Aug. 21, 1991, abandoned, and Ser. No. 2,395, Jan. 13, 1993, abandoned.

[51] Int. Cl.$^6$ .................................................. A61K 48/00
[52] U.S. Cl. ........................... 514/44; 514/924; 514/934
[58] Field of Search ................................ 514/44, 924, 934

[56] References Cited

U.S. PATENT DOCUMENTS

| | | |
|---|---|---|
| 4,649,134 | 3/1987 | Bonomini . |
| 4,693,995 | 9/1987 | Prino et al. . |
| 4,795,744 | 1/1989 | Carter . |

FOREIGN PATENT DOCUMENTS

| | | |
|---|---|---|
| 0025766 | 3/1981 | European Pat. Off. . |
| 0152148 | 8/1985 | European Pat. Off. . |
| 264926 | 11/1987 | Germany . |
| 1187830 | 4/1970 | United Kingdom . |

OTHER PUBLICATIONS

Sullenger et al (1990) Cell 63, 601–608.
Ferrero et al., Chemical Abstract No. 109(13):104533m, 1988.
Marni et al., Chemical Abstract No. 114(7):55511v, 1990.
Bilsel et al., 1990, Interaction of $^3$H–defibrotide with cultured human umbilical vein endothelial cells, *Thrombosis Research*, 58(5):455–460.
Cook et al., Chemical Abstract No. 99:52230p, 1983.
Girard et al., Chemical Abstract No. 96:168754e, 1982.
Gendelman et al., Chemical Abstract No. 113:170225w, 1990.
Merck Index 11th Ed., 1990, p. 192 (#1244—Biotin) and 449 #2851—Defibrotide).
Bonomini et al., 1986, *Haemostatsis*, 16 (suppl. 1):48–50.
Sabba et al., 1988, *Internat'l J. Clin. Pharma., Therapy and Toxicol.*, 26(5):249–252.

*Primary Examiner*—Deborah Crouch
*Attorney, Agent, or Firm*—Banner & Witcoff, Ltd.

[57] ABSTRACT

Oligonucleotides, polynucleotides and derivatives thereof, such as defibrotide, are agents of genetic modulation at the levels of transcription, translation, secondary messengers and cellular signal transduction systems. Such agents can be used to treat HIV infection. Preferably, treatment involves modifying the dose of such agents in response to observed fluctuations (e.g., increase, decrease, appearance, disappearance) in normal, disease and repair markers.

17 Claims, 6 Drawing Sheets

METHOD OF TREATING HIV INFECTION AND RELATED SECONDARY INFECTIONS WITH DEFIBROTIDE

This application is a continuation-in-part of application Ser. No. 07/748,277, filed Aug. 21, 1991, abandoned and application Ser. No. 08/002,395, abandoned filed Jan. 13, 1993.

FIELD OF INVENTION

The invention relates to a method of using sequence non-specific polydeoxyribonucleotides, oligodeoxyribonucleotides and/or derivatives thereof, such as defibrotide, to treat human immunodeficiency virus (HIV) infection. In particular, this invention relates to treating HIV infection, including secondary infections associated therewith with defibrotide.

BACKGROUND OF THE INVENTION

HIV infection is characterized by a progressive decline in immune system function, suppressing the infected host's ability to overcome other, secondary infections. No cure has been found for HIV infection. The pathogenetic process in HIV infection is never unidimensional but, rather, extremely complex and multifactorial. The pathogenic progression may be only tangentially related to the direct infection of a given target cell. Fauci, 1993, Science 262: 1011–1018. Death is inevitable, usually from an overwhelming secondary infection and/or HIV related neoplasm.

Current treatments for HIV infection attempt to retard the progress of the disease or relieve symptoms. Treatments in use today include certain dideoxynucleosides such as azidothymidine (AZT or zidovudine, Burroughs-Wellcome), dideoxyinosine (ddI, Bristol-Myers Squibb) or dideoxycytidine (ddC, Hoffman-LaRoche). These agents can be toxic. Their applicability is limited because of the appearance in some patients of onerous, and sometimes lethal, side effects. These side effects include myelosuppression, peripheral neuropathy, and pancreatitis. In some patients, AZT has lost its effectiveness after prolonged use. While many other drugs have been proposed for treatment of HIV infection, none have been demonstrated to be effective.

Defibrotide is a polyanion salt of a deoxyribonucleic acid obtained from mammalian tissue. Defibrotide is a single-stranded polydeoxyribonucleotide with molecular weight of approximately 20 kDa (low molecular weight form) which may be obtained from bovine lung DNA by controlled hydrolysis. Patents related to its manufacture include U.S. Pat. No. 3,770,720 directed to a process for extracting DNA from mammalian tissue, and U.S. Pat. No. 3,899,481 directed to a process for the controlled partial degradation of DNA extracted from animal organs.

Defibrotide is noted primarily for its profibrinolytic effects (Pescador et al., 1985, Thromb. Res., 30: 1–11). Defibrotide increases the release of tissue-type plasminogen activator (t-PA) and decreases plasminogen activator inhibitor (PAI1) activity. The increase in t-PA is in conjunction with the decrease in PAI1, the latter being the more prominent action. The profibrinolytic activity of defibrotide is likely due to a decrease in PAI1 levels rather than to an increase in t-PA level (Pogliani et at., 1987, Farmaci E Therapia IV, (2): 1–5; Ulutin et al., International Scientific Symposium on Fibrinogen, Thrombosis, Coagulation and Fibrinolysis, Aug. 30–Sep. 1, 1989, Taipei, Taiwan, ROC).

U.S. Pat. No. 3,829,567 is directed to the use of an alkali metal salt of a polynucleotide or an oligonucleotide of ribonucleic acid (RNA) and/or deoxyribonucleic acid (DNA) as a fibrinolytic agent. U.S. Pat. No. 4,649,134 is directed to a method of treating acute renal insufficiencies accompanied by thrombotic microangiopathy with defibrotide. Such pathologies include hemolytic uremic syndrome (HUS), collagenopathies (e.g., panarteritis and lupus), Wegner, Schoenlein-Henoch, disseminated intravascular coagulation (DIC), fast evolving glomerulonephritis, and thrombotic thrombocytopenia purpura (TPP). U.S. Pat. No. 4,693,995 is directed to a method of treating acute states of myocardial ischemia and infarction with defibrotide.

While the primary target cell of defibrotide action has been shown in numerous studies to be the vascular endothelial cell (Bilsel et al., 1990, Thromb. Res., 58: 455–460), cytotropic actions have been shown for hepatic and myocardial cells as well (Lobel and Schror, 1985, Naunyn-Schmiedeberg's Arch. Pharmacol., 331: 125–130).

Defibrotide has been found to be a prostaglandin $I_2(PgI_2)$ secretory agent (Niada et al., 1982, Pharmacological Res. Comm., 14: 949–957). Defibrotide also induces synthesis of other prostanoid metabolites, such as prostaglandin $E_2(PgE_2)$. The increase in secretion of the prostanoid metabolites, in particular $PgI_2$ and $PgE_2$, from vascular endothelial cells seems to involve interaction with arachidonic acid metabolites (Costantini et al., 1989, Eur. J. Int. Med., 1: 115–120). It has been shown in rabbits that prostanoid neosynthesis induced directly by arachidonic acid was significantly enhanced by the stimulation of adenosine $A_1$ and $A_2$ receptors by defibrotide, especially at those levels that do not directly affect the output rate of $PgI_2$ and $PgE_2$ from the rabbit aorta vascular endothelial cells (Ulutin et al., International Scientific Symposium on Fibrinogen, Thrombosis, Coagulation and Fibrinolysis, Aug. 30–Sep. 1, 1989, Taipei, Taiwan, ROC). $PgI_2$ and $PgE_2$ promote microcirculatory vasodilation and antagonism of platelet aggregation. Defibrotide induces an in vivo increase in platelet cyclic adenosine monophosphate (cAMP) levels resulting in aleaggregation of platelets and plasma prostanoid levels, as shown in humans (Cizmeci, 1986, Haemostasis, 16 (suppl. 1): 31–35). Defibrotide does not increase levels of malonylaldehyde, thromboxane $A_2$, thromboxane $B_2$, $\alpha_2$-antiplasmin, or $\alpha_2$-macroglobulin activities.

Defibrotide is also known to exhibit antithrombotic actions (Niada et al., 1981, Thromb. Res., 23: 233–246). Defibrotide has been shown to elevate Protein CA and Protein CI levels, which affects antithrombotic action. The reported elevations in the levels of Protein CA and Protein CI are proposed to be via defibrotide's modulatory effects on the vascular endothelial cell-thrombomodulin levels. At the dose levels utilized thus far, it is devoid of anti-coagulant effects (Coccheri et al., 1982, Int. J. Clin. Pharm. Reg., 11(3): 227–245), and no clinical applicability as an anticoagulant agent has been taught heretofore.

Defibrotide exhibits a synergistic action with, and potentiates the effect of heparin (Ulutin et al., International Scientific Symposium on Fibrinogen, Thrombosis, Coagulation and Fibrinolysis, Aug. 30–Sep. 1, 1989, Taipei, Taiwan, ROC). The synergistic mechanism between defibrotide and heparin is not totally clear. One proposed theory is that defibrotide competitively binds with heparin receptors, promoting prolonged circulation of endogenous heparin. Ulutin et al. reported an increase in anti-Factor Xa activity (Ulutin et al., International Scientific Symposium on Fibrinogen, Thrombosis, Coagulation and Fibrinolysis, Aug. 30–Sep. 1, 1989, Taipei, Taiwan, ROC). This effect may add to its antithrombotic action.

In a comparable animal model of the rat aortic strip, defibrotide was shown to inhibit endothelin-induced contraction of the vascular smooth muscle (Fareed et al., 1990, In: *Advances in vascular pathology*, Elsevier Science Publishers B. V., pp. 171–177). This implies that factors other than impaired fibrinolysis were being treated by defibrotide, such as defibrotide-induced suppression in the levels of the vasoactive amines secreted from the vascular endothelial cells in response to injury. In umbilical vein human endothelial cell cultures, defibrotide was shown to increase cell number and protein content in the culture supernatant, implying a greater role in translation than in the induction of mitotic activity (Bilsel et al., 1990, *Thromb. Res.*, 58: 455–460).

Additional data on defibrotide reveals that defibrotide can modulate lipid peroxidation of membrane phospholipids and oxygen radical induced inhibition of the cyclooxygenase pathway, two major mechanisms in the process of vascular endothelial cell injury. Analogous to these are defibrotide-induced inhibition of superoxide generation by neutrophils induced from platelet activating factor (PAF) (Cirillo et al., 1991, *Haemostasis*, 21: 98–105). Defibrotide has shown protective effect in mice against pulmonary embolism, analogous to the free radical scavenging enzymes superoxide dismutase and catalase (Niada et al., 1986, *Haemostasis*, 16 (suppl. 1): 18–25; Bonomini et al., 1985, *Nephron*, 40: 195–200). Defibrotide-based antithrombotic action in pulmonary embolism may be analogous to the antioxidant effects of cardiovascular drugs.

The cytotropic effects of defibrotide are proposed to be on the basis of $PgI_2$-induced vasodilatation of the microvasculature and the secondary increases in the tissue oxygenation and nutrition. While it has been reported that defibrotide acts via modulation of vascular endothelial cells, its recently formally adopted pharmaceutical classification as a "polypharmaceutical agent" is uniformly ascribed to defibrotide's $PgI_2$ secretory action.

Pre-clinical and clinical experience with defibrotide as well as ex vivo and animal studies done over the past ten years in Europe evidences a cyto-protective effect in myocardial warm and cold ischemia (increased tissue ATP, ADP, 2–3DPG, NADP/NADPH levels), and in reperfusion injuries in the ischemic myocardium and liver (decreased lactate, CPK, intracellular pH), as well as organ procurement and transplantation, proving its cyto-protective effects in other cell types such as myocardial and, hepatic cells (Niada et al., 1986, *Haemostasis*, 16 (suppl. 1): 18–25; Berti et al., 1990, *Advances in Prostaglandin, Thromboxane, and Leukotriene Research*, 21: 939–942). The anti-ischemic effect-induced salvage of the cellular energy pools were ascribed to adenosine receptor induced stimulation of adenylate cyclase enzyme pathway.

Defibrotide therapy has been used in disease states in which inappropriate production or intravascular deposition of fibrin has been a prominent factor. Peripheral obliterative vascular disease (POVD) comprises its primary commercial application in Europe (Ulutin, 1988, *Semin. Thromb. Hemost.*, 14(suppl 1): 58–63), accompanied by the secondary clinical indications of prophylaxis of perisurgical deep vein thrombosis (DVT), and by its less well established use in hemodialysis. Clinical application has been investigated in vasculitides (Raynaud's disease (humans)), prolongation of graft survival in renal transplantation (humans), DIC (animal models), sepsis (animal models), stroke (animal models), renal failure and thrombotic microangiopathy (HUS, TTP (humans)) (Bonomini et al., 1985, *Nephron*, 40: 195–200; Vangelista et al., 1986, *Haemostasis* 16 (suppl. 1): 51–54; Oral et al., 1989, *Blood* 74(suppl 1): 4111a). Defibrotide has been administered to humans primarily as an investigational agent in the United States.

Defibrotide is manufactured by CRINOS Farmacobiologica S.p.A., Villa Guardia (Como), Italy, and is currently marketed only in Italy. Defibrotide, obtained from CRINOS for investigational purposes and clinical trials in the United States, is available in ampules containing 200 milligrams for parenteral administration and in tablets containing 400 milligrams for oral administration.

Although verifiable data indicates that defibrotide, as a nucleic acid, is not toxic, mutagenic or harmful to fetal or embryonic development, maximum dosages of defibrotide administered to humans have been limited to either a body weight-dependent dose of 10–30 milligrams per kilogram, to an empirically established dose of 5.6 grams per day, intravenously, or a fixed dose of 800 milligrams per day, intravenously or by mouth. Coccoheri and Biagi (*Cardiovascular Drug Reviews*, 1991, 9(2): 172–196) report the highest dose of 2.4 to 5.6 grams daily which was given for three days only. These doses, which were based on previous animal studies, were administered empirically. Defibrotide was administered in conjunction with conventional therapy and produced modest advantage.

The pharmacodynamic effect obtained with oral administration of defibrotide is approximately one-half that of parenteral dosing (Fareed et al., 1988, *Seminars in Thrombosis and Hemostatis*—Supplement, 14: 27–37). The maximum dosages of oral defibrotide reported was 1600 milligrams per day. Even at these dosages, clinical improvement was much slower with the oral form of defibrotide than with the parenteral form.

Studies in human pharmacology have been conducted on the same non-dynamic, merely descriptive, principles as the pre-clinical studies, i.e., merely confirming the molecular events induced by defibrotide at pre-determined, set dose levels, uniformly assessed on the principles of using a "minimum efficacious dose." In healthy volunteers, 1200 mg/2 hours was reported to induce increases in the levels of 6-keto $PgF_{1\alpha}$ and $PgE_2$ (not confirmed subsequently by other investigators) (Gryzlewski R. J. et al., *Eicosanoids*, 1989, 2: 163–167), and 1200 mg/day for 2 weeks induced production of prostanoids and inhibition of arachidonic acid 5-lipoxygenase products, the latter known to contribute to pathogenesis and evolution of ischemic tissue damage.

The pro-fibrinolytic effect in healthy volunteers was confirmed by the administration of a single 400–600 mg dose with shortening only in euglobulin lysis time. Administration to peripheral obstructive vascular disease (POVD) patients in dose levels of 800 mg per day given orally, or 200, 400 and 800 mg per day given intramuscularly, displayed an additional effect of decreased PAI1 levels. Conversely, a more recent study failed to show significant activation of fibrinolysis in normal volunteers. A repeat study of POVD patients confirm significant defibrotide induced declines in PAI1 levels (Coccoheri and Biagi, 1991, *Cardiovascular Drug Reviews*, 9(2): 172–196). As a whole, the fibrinolytic effects in healthy volunteers were in general not reproducible, but in patients fibrinolytic effects were reproducible.

In direct opposition to its remarkable potentials in animal models and in vitro/ex vitro systems, published clinical studies with defibrotide have been notable for their modest-to-equivocal results in the respective areas of clinical application. One study continued intravenous defibrotide therapy for as long as three months ("Clinical Effectiveness of Defibrotide in Vaso-Occlusive Disorders and Its Mode of Actions", O. N. Ulutin, M.D. Thieme, Medical Publishers, Inc., *Seminars in Thrombosis and Hemostasis*—

Supplement, Vol. 14, 1988). The majority of the remaining studies administered intravenous defibrotide for only two to three weeks, followed by the administration of oral defibrotide for a period of days to up to six months. Most studies ended at the discontinuation of defibrotide administration. Only one study followed patients for up to three years, although defibrotide was given for only three months ("Defibrotide: An Overview of Clinical, Pharmacology and Early Clinical Studies", Umberto Cornelli, M.D. and Marco Nazzari, M.D., Thieme Medical Publishers, Inc., *Seminars in Thrombosis and Hemostasis*—Supplement, Vol. 14, 1988). More recently, in a double-blind, randomized study conducted in peripheral arterial disease, defibrotide was administered orally for six months. Nearly all clinical studies (thus far) have focused on the agent's profibrinolytic and antithrombotic effects.

In summary, defibrotide has been shown in the art to have antithrombotic, thrombolytic, cytotropic, nephroprotective, platelet deaggregatory and anti-shock properties. These properties have been ascribed to its capacity to release $PgI_2$ or its stable analogues from vascular endothelium. Defibrotide has also been shown to increase t-PA, decrease PAI1, increase protein S and C levels, increase ATIII (unconfirmed reports), increase platelet cAMP levels and, more recently, decrease endothelin-I levels and increase EDRF (endothelium derived relaxing factor) in in vitro models. The art has not recognized that alkalai salts of deoxyribonucleic acid, such as defibrotide, may be useful in the treatment of HIV infection.

In all studies heretofore reported, a particular patient's condition was assessed by using the subjective and objective clinical signs and symptoms of the patient. To date, laboratory results, such as various coagulation assays have been used only to determine the safety and efficacy of defibrotide treatment but not to tailor the therapeutic dose to the individual patient's disease entity or the disease severity or response to prior treatment. Escalating dose levels were never attempted and/or evaluated. Rather, the art has assumed that side-effects will occur when defibrotide is administered in amounts exceeding the "minimum efficacious dose."

SUMMARY OF THE INVENTION

The invention is directed to the treatment of HIV and accompanying opportunistic infections. HIV is characterized by the compromise and/or absence of normal cell functions.

It is an object of the invention to provide a method useful in treating HIV infection and/or secondary infections associated therewith, such as tuberculosis, Herpes virus infection, candidiasis, cryptococcal diarrhea, arthralgia and chronic waste syndrome.

To accomplish this objective, the invention provides a method of treatment comprising administering to a patient which has been infected by HIV an effective amount of one or more sequence nonspecific nuclcic acids selected from the group consisting of polydeoxyribonucleotides, oligodeoxyribonucleotides and derivatives thereof.

Preferably, the method is practiced in a marker dependent manner, which method of treating HIV and/or secondary infection comprises:

(a) determining the initial state of a set of disease markers, the disease markers being observable characteristics of a patient which deviate from the normal condition due to the disease state and wherein each disease marker in the set has a predetermined reference range which is indicative of the normal condition, (b) administering to the patient a dose of a therapeutic compound comprising one or more sequence nonspecific nucleic acids selected from the group consisting of polydeoxyribonucleotides, oligodeoxyribonucleotides and derivatives thereof, (c) selecting a repair marker, the intensity of which increases following administration of the therapeutic compound, where intensity is the extent to which the state of the repair marker differs from its state in the normal condition, the repair marker being the concentration of a compound which participates in a cellular regulatory pathway which operates through protein kinase A, protein kinase C, or G-protein, (d) administering the therapeutic compound at a dose level incrementally higher than the previous dose, (e) repeating step (d) each time the intensity of the repair marker increases following an incrementally higher dose, (f) repeating steps (d) and (e) until the intensity of the repair marker in step (c) no longer increases, (g) administering the therapeutic compound at the highest dose level attained in step (f) until the intensity of the repair marker returns to the normal condition, and (h) administering the therapeutic compound at a dose level incrementally higher than the previous dose and repeating steps (c), (d), (e), (f) and (g) with one or more additional repair markers until all disease markers of the set of disease markers no longer deviate from the normal condition.

The patient is monitored weekly for three or more weeks. If relapse occurs, as indicated by a deviation of one or more disease and/or repair markers from the normal level, therapy is reinitiated at the highest dose level of the prior course of therapy until normalization is again reached.

In a particularly preferred embodiment of the invention, the method of treating HIV and/or associated disease comprises the steps of:

(a) determining the initial state of a set of disease markers, the disease markers being observable characteristics of a patient which deviate from the normal condition due to the disease state and wherein each disease marker in the set has a predetermined reference range which is indicative of the normal condition, (b) administering to the patient a dose of a therapeutic compound comprising one or more sequence nonspecific nucleic acids selected from the group consisting of polydeoxyribonucleotides, oligodeoxyribonucleotides and derivatives thereof, wherein the dose of the therapeutic compound is at a level which raises a universal marker to at least five times its normal level, the universal marker being a constitutively expressed molecule which is transcriptionally activated by the therapeutic compound in all disease status, and (c) continuing to administer the therapeutic compound at the dose level of step (b) until the universal marker returns to its normal level.

In the treatment of HIV, not only levels of those molecules misproduced by the normal cell, but also molecules produced by infected cells are assayed, e.g. , viral encodal proteins. Cell cultures and other conventional tests are performed to detect the presence and activity level of virus and viral related components. The method includes titration of the dose to concurrently reestablish normal cell functions and neutralize and eliminate infectious viral particles.

The invention also provides a method of gene therapy wherein a sequence specific nucleic acids corresponding specifically to selected parts of the viral genome or transcriptional factors is administered with the sequence nonspecific nucleic acid such as defibrotide or analog thereof, preferably in incrementally higher dose levels in a marker dependent manner.

The invention contemplates treating HIV infection in which HIV is not expressed and wherein the concentration of at least one immunological molecule, such as CD4, CD25, IL-1, IL-3, IL-4, IL-6, TNF and sIL2R, is followed. The method comprises:

(a) administering to the patient an effective amount of a therapeutic compound comprising one or more sequence nonspecific nucleic acids selected from the group consisting of polydeoxyribonucleotides, oligodeoxyribonucleotides, and derivatives thereof, wherein the effective amount is the amount which causes a universal marker to rise at least five times its normal level, the universal marker being the concentration of a constitutively expressed molecule which is transcriptionally activated by the therapeutic compound in all disease states, and (b) continuing to administer the effective amount of the therapeutic compound until the universal marker returns to its normal level.

DETAILED DESCRIPTION OF THE INVENTION

Figure 1:
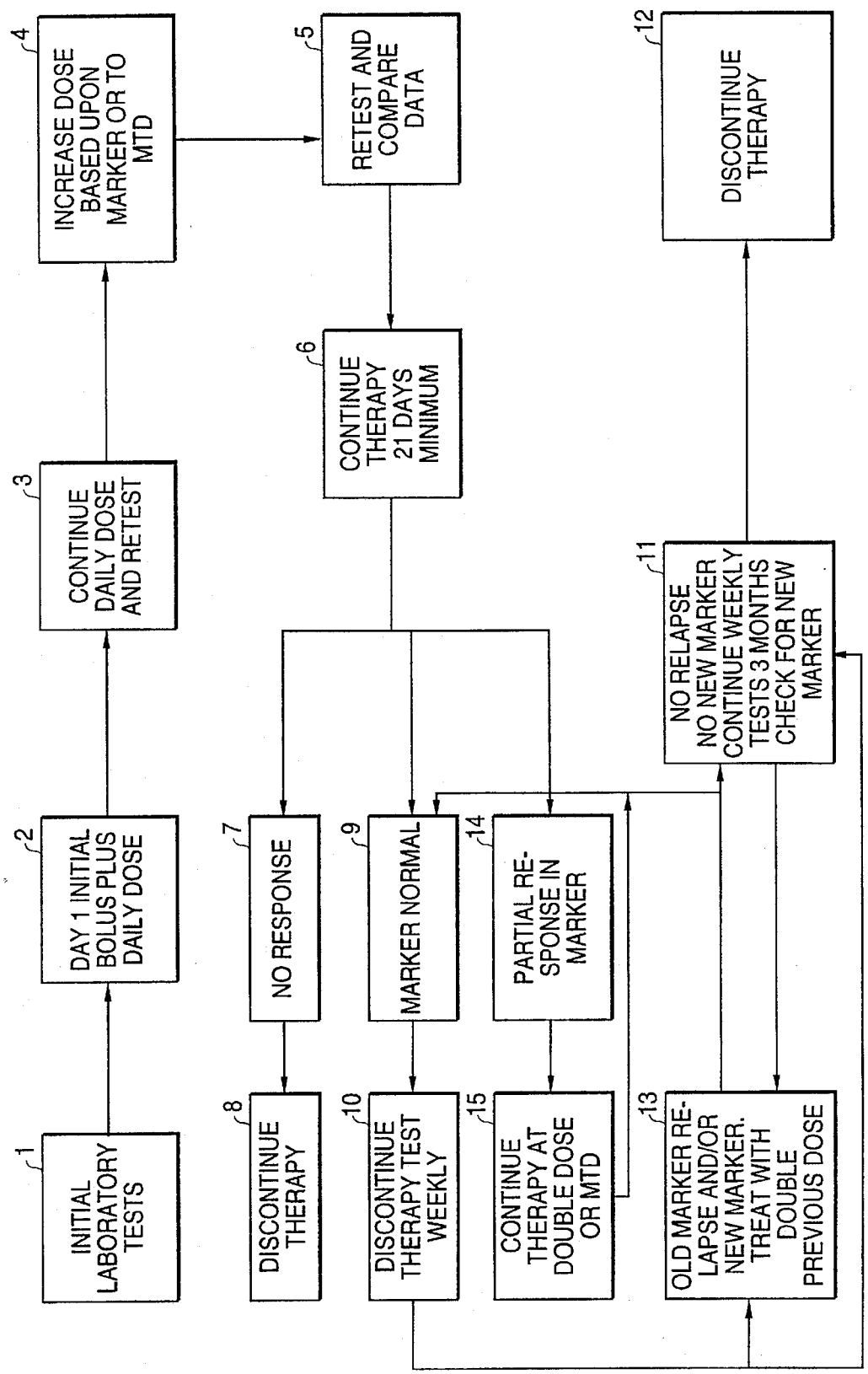
FIG. 1 is a diagram schematically illustrating a preferred embodiment of the invention.

AIDS virus can manifest itself in four basic stages which are well known in the art and described in the medical literature: 1) HIV positive (HIV⁺) blood test but otherwise no abnormal laboratory findings or clinical symptoms; 2) pre AIDS Related Complex (pre-ARC); 3) AIDS Related Complex (ARC); and 4) Active AIDS. The last three stages may be present in combination with other infections, with central and/or peripheral nervous system disease, with associated autoimmune disease or with related neoplasm. All four stages are treatable using the same basic method described herein.

This invention provides a method for the therapeutic multiphase application of therapeutic compounds which are sequence nonspecific polydeoxyribonucleotides, oligodeoxyribonucleotides, and/or derivatives thereof, including but not restricted to defibrotide, in the treatment of HIV including the debilitating symptoms of secondary infections.

It has been discovered that therapeutic nucleic acids such as defibrotide can be used, and in a manner not heretofore employed in the art, to manage HIV infection and associated opportunistic infections. Opportunistic secondary infections include herpes, cryptococcal diarrhea, scleroderma, arthralgia and tuberculosis. Specifically, it has been discovered that the debilitating symptoms of secondary infections wane upon treatment with defibrotide.

Mycobacterium tuberculosis, the agent of tuberculosis (TB) is a deadly pathogen. TB remains the leading cause of death in the world from a single infectious agent. While the risk of TB infection in the United States had been declining over the past century, the incidence of TB is now increasing. The increased number of TB cases is attributable in part to the result of HIV and TB co-infection. *Science*, 1992, 257: 1055–1064. AIDS patients often exhibit TB as a presenting opportunistic infection. TB occurring with HIV infection is a serious and growing public health problem. *The Lancet*, 1993, 342: 268–272.

It has now been discovered that the administration of sequence non-specific DNA, such as defibrotide, decreases IL-1, IL-2, TNF-α and IL-6, all of which are known inducers of HIV proliferation. Administration of such an agent also increases total lymphocyte and T-lymphocyte counts, CD4 counts, and CD8 counts, as well as increasing cGMP/cAMP ratios to proportions seen in normal laboratory controls. An anabolic effect has also been observed.

Preferably, the deoxyribonucleic acid is administered in a marker dependent manner. A "marker" is an observable characteristic of the patient which may be observed directly by the clinician or determined by diagnostic procedures. The state of an individual marker is correlatable with the status of the disease or repair processes in the patient. Dosing of the therapeutic nucleic acids according to the method of this invention is based on changes in the status of these markers as taught herein.

Treatment of HIV and related disease states in accordance with the preferred method of the invention involves the administration of the therapeutic nucleic acid or derivative at a daily dose level sufficient to increase the intensity, determined as concentration or clinical observation, of a marker of cellular repair processes ("repair marker") to a plateau level (i.e., where the intensity of the marker is not changed by continued administration of the therapeutic compound). This daily dose level is the "maximum efficacious dose" for the particular disease and repair marker. Administration of the therapeutic compound is continued at the same dose level until the repair marker stabilizes by returning to the normal level.

If at least one disease marker remains in an abnormal state, the daily dose level of the therapeutic compound is increased. At least one other repair marker will increase in intensity, and the daily dose level is increased until the intensity of the new marker reaches a plateau level. Administration of the therapeutic compound is continued at this new maximum efficacious level until the respective repair marker stabilizes at the level and proportion assessed in normal laboratory controls.

When all disease markers have returned to the level of the normal state, administration of the therapeutic compound is discontinued, but the levels of the disease and repair markers are monitored every three weeks, for an additional 3–6 months. If the levels of all markers remains at that of the normal state, cure has been achieved. If any marker deviates from normal at the end of any three week period, administration of the therapeutic compound is resumed at the highest "maximum efficacious dose" that has been used during the immediate prior treatment, and the new maximum effective dose is established by the known methodology.

A system of dose assessment and completely new dose levels based on the concepts herein discussed has now been developed. Since therapeutic nucleic acids such as defibrotide act to revive normal cell function, and acts as an immunosuppressant of inappropriately or disproportionately activated cellular repair events, dose and duration of therapy must be modified individually per patient or disease depending on the function, type, and degree of cell injury. Second, defibrotide and other nucleic acids are cell modulators. In this regard, nucleic acids such as defibrotide and derivatives thereof have now been recognized as the only class of agents committed to restoration of normal cell function. In itself, this effect of the therapeutic compound is incompatible (in a state of cure) with an "over-functional" state, i.e. any complications caused by the therapy. Hence, dose levels higher than the "minimum efficacious dose" used in the prior art will be complication free. Third, defibrotide has now been recognized to be a member of a new class of pharmaceutical agents that will act via activation of respective cell functions with varying polypharmacological actions that are disease specific, induced by varying dose levels of defibrotide. Fourth, this class of agents have to be administered at escalating dose levels until and when maximum clinical benefit is observed. Therapy with these agents requires the development of the "maximum efficacious dose" principle for the assessment of therapeutic dose levels, thus eliminating the heretofore universally applied principle of "minimum efficacious dose." Fifth, this class of agents represent the only polypharmaceutical agents of their kind which exert their therapeutic effects not by their direct molecular actions, but by activating (in the diseased cell) the selected polypharmacological events of the recovery process.

"Pleiotropism" as used herein, is defined as the tissue and cell specific expression of cellular genomes via phosphorylation of the enzymes, via reinstitution of cell-surface receptor ligand interactions, protein kinase A and protein kinase C pathways as well as second messengers of cAMP, $Ca^{2+}$, diacylglycerol (DAG), and 1,3 phosphoinositol which may under- or over-regulate the genomic transcriptional/translational activities.

The term "maximum efficacious dose" is defined herein as the daily dose rate, that will elicit, in nearly 100% of treated patients, the reversal of the respective disease markers to the uniformly normal level, and establishment of normal cellular markers. The maximum efficacious dose is usually expressed as amount of therapeutic compound administered per kilogram body weight per day (DKGD). The maximum efficacious dose represents a novel concept of administering a pharmaceutical agent in therapeutic medicine.

The term "maximum therapeutic dose" is defined herein as the total cumulative dose (the daily dose summed over the duration of administration) that will elicit in nearly 100% of treated patients the irreversible and complete normalization of the respective disease markers and resumption of normal cellular functions, i.e., the state of cure.

The term "minimum efficacious dose" is used herein to refer to the dose used in the heretofore universal practiced method of administering a pharmaceutical agent. The minimum efficacious dose is the dose (daily dose or steady state level) that will elicit a particular pharmaceutical action in a certain percentage of patients, without inducing the pleiotropism of the whole repair process.

Pharmacological agents have heretofore been administered at set dose levels (i.e., the "minimum efficacious dose") to treat the gross pathology and discontinued when complete or partial remission of the gross pathology was achieved. The object of the invention is to achieve complete remission of each disease stage. Treatment according to this invention begins at the gross pathology stage which has one or more associated markers. Normalization or improvement of those markers indicate that the treatment is beneficial. In conventional treatments of disease, treatment is stopped after a certain period of time at a set dose level, usually corresponding to complete or partial remission of the disease indicators of gross pathology. However, such a remission is not the event which causes discontinuation of therapy in accordance with this invention. Normalization of the markers of gross pathology indicates, rather, that a disease state corresponding to a lower level of disease activity has been reached. Markers of that stage (i.e., the lower level of disease activity) are identified and treatment is continued to normalize those markers. Complete cure is reached only if all stages of the revival process are treated.

The term "maximum tolerable dose," as used herein, is defined as the highest daily dose that can be administered without any complications, e.g., no bleeding complications or thrombopathy, etc. This in fact has been the sole and primary side effect of the high-molecular weight nucleic acid (defibrotide) utilized in the studies reported herein, i.e., the antithrombotic effect inducing bleeding complications at 300 mg/kg/day dose or above. If the maximum efficacious dose should be higher than the maximum tolerable dose, chemical modification of the nucleotide for more efficacious transmembrane transport and cellular entry would be necessary.

It has been determined that the therapeutic nucleic acid will not indefinitely increase transcriptional activity with increasing doses. In this regard, transcriptional activity will shut off when the repair molecules are no longer needed, i.e., when no more "injury signal" is transmitted via stimulation of adenylate cyclase, second messengers, etc. In contrast, no matter how high the dose range in the normal individual may be, there is no induction of transcriptional activity (as indicated by, e.g., elevation in the yon Willebrandt antigen (vWAg) levels). This supports the fact that no complications are seen with therapy using nucleotides which modulate cellular repair mechanisms for a therapeutic effect. For example, tissue plasminogen activator antigen (AgTPA) will not continue to rise indefinitely with increasing doses but will increase only in the presence of injury and at the locality of the injury, e.g., the existence of a thrombus which inevitably will be associated with the endothelial cell of the locality specific lesion. Hence no bleeding complications are to be seen secondary to systemic induction of the therapeutic compound at physiological dose ranges beyond the upper limits of the prior art thrombolytic therapy.

This mechanism is supported by the way the cell modifies activation of the repair process. As is well known, 50% occupation of cell surface receptors will lead to 50% increase in the baseline level of intracellular cAMP, 100% occupation of cell surface receptors will lead to a 100% increase in the intracellular cAMP level. This will correspond to 5 times the elevation of the baseline vWAg level.

Phosphorylation of various different transcriptional factors simultaneously will lead to concurrent tissue specific turning on or off of the respective transcriptional factors, e.g., some molecules are turned on and some are turned off. This constitutes the pleiotropism of the nucleic acids as herein defined.

Treatable Disease States

HIV and any disease state characterized by injury-based alteration in the production, expression or activity of compounds whose production, expression or activity is regulated by the cell at least in part through cell surface receptors such as Adenosine $A_1$ and $A_2$, collagen, thrombin, epinephrin and norepinephrine receptors, through the protein kinase A or protein kinase C pathways, or by protein factors whose phosphorylation affects genomic translation and transcription may be treated with defibrotide in a marker dependent manner as described herein.

Treatable disease states include those having an abnormal genomic component, such as the primary HIV infection, as well as secondary infections occurring therewith which may or may not have an abnormal genetic component.

Diseases with an abnormal genomic component are characterized in that one factor in the disease process is the expression of an abnormal DNA sequence related to the disease. Such sequences may include viral genomes and transformed genes such as activated oncogenes. While the method of this invention will result in the return of normal cellular function in the diseases with an abnormal genomic component, a complete cure as defined herein will not remove the abnormal DNA sequence solely by administration of the therapeutic nucleotide compound. As taught herein, the preferred method for treatment of disease states with an abnormal genomic component contemplates adding to administration of the therapeutic nucleotide compound a coupled treatment directed at eliminating disease-related DNA sequences, for instance by removing the genomic defect.

Diseases with no abnormal genomic component are those diseases within the broad definition of diseases treatable by the method which do not involve expression of an abnormal DNA sequence. Complete cure can be achieved in diseases with no abnormal genomic component solely by administration of the therapeutic compound as described herein. It is within the contemplation of this invention to administer the therapeutic compound either alone or contemporaneously with other therapy directed to the particular disease proce It should be recognized that the other therapies are intended to force non-normal cellular function, and therefore they are likely to extend the time required for therapy with the therapeutic nucleotide compounds to achieve a return to normal cellular function.

The inventors have discovered that in addition to HIV and infections associated therewith, other disease states involving cell malfunction of, for example, vascular endothelial cells, the cellular components of parenchymal tissue damage involving the kidney, heart, liver, etc., any disease state involving malfunctioning of the blood vessels, circulating blood cells, disease states of the central, peripheral and autonomic nervous systems and viral diseases involving reversible genetic modulation of the immune cells not excluding infestation of the tissue cells of the involved organs may be treated with defibrotide and its derivatives. Such diseases include, but are not limited to POVD, DVT, DIC, thrombotic microangiopathies (e.g., HUS, TTP); renal failure; nephrogenic hypertension; consumptive thrombocytopenia, acquired thrombopathy and hemolysis; immunosuppression; autoimmune diseases such as rheumatoid arthritis; post-phlebitic syndrome; tissue necrosis with or without proximal vascular occlusion; acute/subacute (subendocardial) myocardial infarction; adult respiratory distress syndrome (ARDS); thrombosis of cranial sinuses; ischemic parenchymal tissue damage; acute myocardial infarction; pulmonary embolism; thrombotic cerebrovascular events; vascular endothelitis (e.g., Kawasaki's disease, polyarteritis nodosa, midline granuloma); scleroderma, Raynaud's disease; inflammatory (autoimmune or otherwise) myositis; inflammatory dermatitis; inflammatory symptoms of systemic lupus erythematosus (SLE) and other collagen vascular diseases; Sjogren's disease; inflammatory bowel disease (IBD); thyroiditis; stasis ulcers; sickle cell disease; pulmonary fibrosis; hypersensitivity pneumonitis; burns; peripheral obstructive arterial disease; septic shock; eclampsia; graft vs. host disease; retrovital diseases including HIV infection, adenoviral; herpetic and other viral infections; hyperimmune states such as chronic fatigue syndrome, solid organ rejection, venoocclusive disease, etc. Since prior art has shown the up-regulation of adenosine $A_1$ and $A_2$ receptors by defibrotide in the nerve cells, it can be inferred that the prototype nucleotide defibrotide and its derivatives may also be therapeutically beneficial in treating diseases of the nervous system.

The methodology described herein has universal application within the scope of disease states characterized by the absence or inadequacy of one or more of those cell functions which are normally regulated through the cell surface receptors listed above, through the protein kinase A or C pathways or by protein factors whose phosphorylation affects gene transcription, so long as the abnormalities in these cell functions are yet still reversible. The methodology is also applicable to the disease states characterized by acquired or genetic dismodulation, and/or transformation. Revival, institution or reinstitution of the normal state of those functions is, by definition, a state of cure. Revival of the normal cell functions can occur where the diseased cell preserves the biological capacity for the physiologically predefined events of the cellular repair functions of the recovery process, if those events are pharmacologically induced by the correct use of the therapeutic nucleic acids. Complete cure is the therapeutic objective. The decisive factor in the success of this therapeutic approach is not only the pharmaceutical agent, but how it is utilized. If the biological capacity for regaining normalcy is there, therapeutic failure is eliminated. This biologically predetermined potential for cure is reproducibly and predictably obtainable, however, only by the correctly determined iatrogenetically controlled dose levels, and duration of therapy. Incorrect dose administration leads to the therapeutically missed event of complete cure. Complete cure, however, is not possible if necessary dose levels cannot be attained without complications such as bleeding or thrombopathy.

While the marker dependent dose methodology is universally applicable, it has been surprisingly discovered that HIV, as well as associated opportunistic secondary infections can be effectively treated with nucleic acids such as defibrotide.

Therapeutic Compounds

The invention uses polypharmacological medical therapy components which are defined by the predetermined biological events of the cellular repair process. The invention defines a previously unidentified class of drugs whose pharmaceutical actions modulate selectively and most effectively the injury specific cellular functions. This class of drugs include defibrotide as well as other nucleic acid derivatives. The pharmaceutical action is guided by the intrinsic biological material of the cell matching specifically and completely the cellular events of the recovery to the exact components of the injury.

The therapeutic compound contemplated for treatment by the method of this invention is an oligomer or a polymer of deoxyribonucleotides or derivatives thereof. The compound may be native or chemically synthesized, or a fragment of a native polydeoxyribonucleotide. The compound has at least three nucleotide residues, and may have up to about 250 residues. Preferably, the nucleotide compound will have from about 15 to about 200 residues, more preferably from about 20 to about 150 residues, most preferably from about 50 to about 75 residues. The sequence of the nucleotide residues in the polymer is not critical, and may include interdisposed sense, anti-sense, non-sense or missense sequences. A therapeutic composition may contain polynucleotide molecules with varying numbers of residues within the range described above. The skilled worker will be able to select an appropriate length (degree of polymerization) based on the ability of the compound to penetrate the cell and on the ability of the compound to cause a change in the level of various repair markers in accordance with the method of this invention.

The nucleic acid compound will preferably be relatively resistant to ecto-and endonucleases. The 3' OH of the terminal residue of the therapeutic compound according to this invention may be phosphorylated or not, and the compound will still function without the need for intracellular phosphorylation. The therapeutic compound according to this invention is a polyanion, and the negative charge is balanced by counter ions. The counter ions may be alkali metal ions or alkaline earth ions, biologic amines or other suitable counter ions which do not interfere with treatment according to the method of this invention. Preferably, at least some of the counter ions are zinc ions. Commercially available defibrotide contains about 10–20 µg of zinc and about 200–250 µg of iodine per gram of defibrotide. The amount of zinc, however, may be increased either be directly incorporating zinc into the nucleotide compound or, alternatively, by administering zinc, e.g., in the form of a dietary supplement, along with the therapeutic nucleotide. Zinc containing compounds may be coadministered with the nucleotide to obtain a ratio of from 2–20 zinc atoms per phosphate group or iodine atom.

Defibrotide is chemically characterized as a polyanionic derivative of deoxyribonucleic acid. While further discussion will be directed to the use of defibrotide as the prototype drug, it is to be understood that other nucleic acids and derivatives are included in the use thereof. Derivatives included within the scope of the invention include nucleic acid, i.e., DNA, which is conjugated with poly(L-lysine) or which is modified by, for example, the addition of amino acids such as lysine, histidine and arginine, the addition of optimum concentrations of folate and/or biotin, the addition of the optimum ratios of metals and ions including zinc, manganese and iodine, by the addition of 5'-polyalkyl moieties, cholesterol, vitamin E, 1-2-di-O-hexadecyl-3-glyceryl and other lipophilic moieties and/or modified by the replacement of phosphodiester bonds with phosphothiotate bonds, and/or modified nucleotide sequences of the prototype nucleic acid, defibrotide.

Verifications of the relative therapeutic unimportance of defibrotide's molecular structure in directly producing its various polypharmacological actions was provided by various means. These included non-uniformity of its various actions in different disease states; differences between the types of various "disease markers" reproducibly and effectively treated by defibrotide; lack of uniformity in the states of responsiveness of the same "disease markers" to the same "dose levels" at different stages of the disease process confirming greater responsiveness of the disease markers to lower dose levels with higher disease activity states and vice versa. This supports the concept that defibrotide's polypharmacological profile is a function of the injury state. The efficacy and the emergence of selected polypharmacological spectrum of actions, in turn, is a direct function of adequately administered dose levels.

While the inventors do not wish to be bound to a particular theory with respect to the mechanism of action of defibrotide, it is believed that treatment with defibrotide leads to the direct modulation of second messenger molecules such as cAMP, cAMP dependent protein kinase A enzymes, adenylate cyclase, G-proteins, the modulation of balancing signal transduction systems of calcium and diacylglycerol pathway, phosphoinositol, and protein kinase C enzymes as well as to the modulation, via cAMP, of phosphoproteins of transcription and translation and cAMP modulated oncogenes such as c-myc, ras, c-fos, c-jun, NK-kB, transcriptional factors and lymphokines such as EIAI, AP-I, COUP, IL-2, IL-6, TCF-1$\alpha$, TATA, and TAT element, and oxygen radical modulation of cAMP response element (CRE) and modulation of CREB and CREM genes, as well as phosphoproteins of transcriptional and translational cellular functions via protein kinase A/C induced phosphorylation of the respective enzymes.

As shown by the data presented herein, derivatives of nucleic acids, such as defibrotide, act upon malfunctioning cells to restore normal cell function. For a given disease certain cell malfunctions may be caused by the disease while other cell functions are normal. Only the malfunctions of the cell will be affected by treatment with defibrotide. Normal functions will not be hindered and/or increased during treatment.

The process of complete cure moves progressively from gross healing at the tissue level to healing at the molecular level, and thereafter, to healing at the genomic level. In order to accomplish a complete cure, therapy must be at the proper maximum efficacious dose and of the proper duration (i.e., maximum therapeutic dose) to eliminate the disease marker, fully induce the repair marker to completion of the repair process, and reinstate the normal cellular marker. Each successive stage of the repair process involves the dose management of all three marker classifications concurrently.

Marker-Driven Therapy

The claimed method involves the use of a "marker dependent dose assessment" methodology for determining the therapeutically most efficacious use of the respective pharmaceutical agents. The use of incremental marker stratification reflects the concept that "maximum efficacious dose" is redefined through the different stages of treatment, each time adjusted to the respective specific marker most representative of the respective pathogenic/clinical picture of the disease state. Treatment at respectively higher doses corresponding to the progressively lower disease activity levels are continued until a state of total cure is reached.

Intrinsic to the claimed method is the total elimination of empirically assessed doses or constant therapy doses, arrived at by the universal pharmaceutical principal of "minimum efficacious dose" for a class of drugs, which, until the present time, has been the standard for the definition of the "effective therapeutic dose." The respective doses thereof are defined to elicit a response corresponding to different disease functions of the treated cell and revival of the respective disease parameters, in a stratified fashion.

The method of treating various diseases provided by this invention uses specific clinical and laboratory markers to assess dosages to be administered. The markers vary from gross clinical observations of pathology to the progressively subclinical yet valid detection of certain laboratory levels associated with a particular disease. The preferred markers are the clinical parameters as well as the molecular products produced, or inhibited, present or absent when cellular events associated with a particular disease occur.

Certain laboratory assays are used to assure that the dosages are safe for the patient being treated. For therapy with defibrotide these may include prothrombin time, activated partial prothromboplastin time, thrombin time, reptilase time, bleeding time, platelet function assays, and coagulation factors. A second set of laboratory assays (i.e., "disease markers") are utilized to indicate the efficacy of the doses. "Repair markers" are used to assess clinical adequacy of dose escalation and duration of therapy.

As defined herein, "normal cellular markers" are molecules of normal cellular function. They are tissue and cell specific and may share common pathways of second messengers or signal transduction pathways and normal cellular genomes. At the genome level, normal cell markers are genes that are constitutively expressed, transcribed, translated and transduced. Establishing dose and duration of therapy based on second messengers, signal transduction pathways and induction of genomic transcription is a novel modality of administering a pharmaceutical agent.

As defined herein, "disease markers" are markers which are induced and defined by the type of disease process. Disease markers are clinical or laboratory parameters that deviate from normalcy. A disease marker may be absent or present, decreased or increased. At the genome level, disease markers are genomes of genetic dismodulation (e.g. viral genome, transcribed oncogenes, mistranscribed genomes); nontranscribed genomes (e.g., familial/genetically absent genomes, under-regulated/suppressed genomes), and/or over-expressed, not appropriately shut off transcriptions of genomes (e.g. activated repair molecules, second messengers and molecules of signal transduction pathways).

Disease markers are observable characteristics of the organism whose status in a disease state differs from the status in the normal (non-disease) state. Such characteristics and their association with their respective disease states are well known to the skilled practitioner. In the practice of the method of this invention, it is contemplated that the practitioner will monitor the status of multiple disease markers related to the disease being treated, either simultaneously or sequentially.

The disease markers include both clinical markers, which are observed directly by clinician, and laboratory markers, which represent quantitative values determined by support staff. These characteristics include, but are not limited to, the concentration of compounds whose production or expression is affected by injury-based alteration of cell surface receptors such as Adenosine $A_1$ and $A_2$, collagen, thrombin, epinephrin and norepinephrine receptors, of protein kinase A or protein kinase C pathways, or of protein factors whose phosphorylation affects genomic translation and transcription, or hybridization of genomic enhancers/inhibitors infusion or excess enhancers, infusion of excess genomes to deplete viral/cellular transactivation transcription factors, etc. where the concentration in the disease state differs from the concentration in the normal state. Disease markers for HIV related disease states include odynophagia, arthralgia, *Herpes labialis, Herpes genitalis*, cryptosparidium diarrhea, Karnofsky performance score, waste syndrome.

The normal state concentration of these markers will be known to the skilled practitioner, and usually represents a range of concentration values determined by measurement of the concentration of the compound in a large number of individuals who are not in a disease state, by the respective laboratory.

Repair markers are compounds that participate in the regulatory pathways which include protein kinase A or protein kinase C. Adenylate cyclase is known to be activated by G-proteins (see Ross, 1992, *Current Biology*, 2(10): 517–519, the disclosure of which is incorporated herein by reference) with eventual production of cAMP and cAMP-dependent activation of protein kinase A, leading to phosphorylation of the respective transcription factors, until 100% of the cell membrane receptors are taken up by the ligands. For defibrotide these receptors are β-adrenergic receptors, collagen receptors, adenosine $A_1/A_2$ receptors, ADP receptors, thrombin receptors, collagen receptors, etc). A parallel pathway operates through activation of protein kinase C, in response to intracellular calcium ion level, inositol triphosphate and diacylglycerol, responsive to ligand binding to another set of receptors and similarly controlling transcription/translation of respective proteins. These pathways, and their intermediate compounds are well known to those skilled in the art. However, their use in assessment of therapeutic dosage have not, heretofore, been known in the art.

In particular, "repair markers" are molecules in the pathways of the respective cellular repair processes defined by the type of injury. Repair markers are transcribed or shut off genes, second messengers and/or molecules of the signal transduction pathways that may be increased, decreased, or absent in response to cellular injury. As discussed herein, the term "repair marker" may refer to the compound or its concentration or the measurement value of an assay associated with the concentration of the compound. The level of a repair marker may deviate from the level present in the cell during normal function, and when it does so deviate, cellular repair processes are activated. This deviation may be positive or negative, depending on the disease state and the precise state of cellular repair currently in progress. As discussed herein, the "intensity" of the repair marker will refer to the degree of deviation from the level during normal cellular function, without regard to whether the deviation is positive or negative. The use of repair markers in establishing dose and duration of therapy is a novel mode of administering a pharmaceutical agent.

As defined herein, a "universal marker" is a constitutively expressed molecule transcriptionally activated by the respective nucleic acid universally in all disease states for which the nucleic acid is specific. "Universal markers" are specific for each nucleic acid employed. While the universal marker is the only molecule that is not injury specific and has no therapeutic value, it is expressive of the event and duration of the ongoing repair process. Transcriptional activation gets shut off with the establishment of the state of cure. As such, the universal marker does not get modulated unless there is a disease state and the respective nucleic acid has therapeutic specificity. The universal marker carries a direct quantitative relationship to the daily per kilogram body weight dose (DKGD) of the nucleic acid employed. A universal marker defined for the prototype nucleic acid (defibrotide) is vWAg. Other "housekeeping genes" related to particular nucleic acids can be selected as per the target cell involved from the respective "housekeeping genes."

Clinical and clinical laboratory markers may be determined through blood tests, urine tests, clinical observation or identification of blood clots by any of several conventional techniques, as well as the more novel techniques of determining genomic transcriptional and translational activity by DNA finger printing, PCR and the like. To evaluate the markers, the laboratory analyses measure levels of certain proteins, lymphokines, enzymes and relevant molecules. Clinical markers include blood pressure, visible tissue damage, signs of inflammation, ecchymoses, and the like. Clinical markers vary from one disease to another. Moreover, like HIV, many diseases progress through several clinical stages during the process of recovery. The clinical markers of one stage of a disease are frequently different from the clinical markers in other stages of the disease, befitting different stages of the pathogenic picture.

The detection of markers relevant to the particular disease, stage of that disease, and as baseline for dose escalation, must first be identified. Any observable characteristic generally accepted by the skilled practitioner as being associated with a specific disease state may be employed as a clinical marker. See, e.g., Harrison's *PRINCIPLES OF INTERNAL MEDICINE*, 10th Edition, Petersdorf et al. Eds., McGraw Hill. The skilled artisan would readily recognize those markers indicative of a pathological state.

One critical marker is chosen at each respective stage of the repair process and the maximum efficacious dose for that marker established. Administration of that dose induces correction of other stage-specific markers not necessarily identified or aimed at during therapy (i.e., "stage specific pleiotropism"). Following normalization of the first chosen marker, a second marker which continues to deviate from the normal condition is chosen. The dose that normalizes the second marker (i.e., the higher dose) is likely to further improve the first marker incrementally.

Initial administration of the selected dosage is followed by incrementally increasing dosages until the "maximum efficacious dose" is reached. A panel of laboratory assays to determine the state of the markers (e.g., absence, increase, decrease) is repeated every 3 to 7 days during therapy. These results together with the clinical markers of disease would indicate whether the defibrotide, or other nucleic acid derivative, is adequate in dose and duration to cause improvement in the pertinent marker or markers while simultaneously being totally safe to administer. Therapy is continued with escalating doses over sufficient time to assure complete normalization (i.e., the clinical laboratory assays, when compared to the reference range, are indicative of the normal condition) of the pertinent markers. When normalization is reached, therapy is stopped.

Although therapy is discontinued, the patient is tested weekly for the current state of the pertinent disease marker. If relapse occurs, therapy is reinitiated at the highest dose level of the prior course of therapy until normalization is again reached. While optional, it is advisable to continue escalating the dose level to potentially reach a shorter duration of therapy.

The highest tolerable dose per day which is complication free (e.g., no bleeding, thrombopathy) is preferred since treatment periods are usually shorter at higher dose levels. Therapy cycles are repeated until there is complete and irreversible normalization of the pertinent markers at which point the patient is cured. A marker is considered to be irreversibly normalized if it remains normal for three months without therapy.

There is a certain dose level which will ultimately give plateau levels on a particular marker, and irrespective of how long the dose range is continued, the level of the molecule will not go higher unless the dose (or cellular uptake of the respective nucleotide) is increased. This agrees with accepted biochemical knowledge, i.e., the more the number of receptors receiving signals, the more cAMP is produced and, as a consequence, the higher the transcriptional activity pertaining to vWAg is.

Minimum effective dosing is therefore counterproductive and markers have to be used to assess the maximum efficacious dose. Application of the higher dose will promptly lead to higher levels in a shorter time (high m-efficiency score). This is confirmed from the cellular uptake curves.

Once a plateau is reached with the maximum efficacious dose, the H-efficiency score can thereafter be used along with the maximum highest levels of the last day to assess how long therapy should be continued to complete the repair process, i.e., when the maximum efficacious dose is continued when m-efficiency score is less than 1.0, the nucleotide no longer exerts any further therapeutic effect. This observation leads to the statistical definition of "maximum therapeutic dose," i.e., the time slot of the total administered dose beyond which further repair of the selected marker would not take place at that particular dose level.

If another disease marker were selected, the maximum efficacious dose and maximum therapeutic dose would be redefined for that second stage marker.

One skilled in the art, based on the information presented herein, would be able to detect and determine finer disease/repair markers so as not to miss complete cure. Any abnormality in any marker should prompt reinitiation of therapy, even if no visible disease markers are observed, since many of the markers of the subclinical stage will be biochemical molecules, e.g., an interleukin.

Treatment in Accordance with the Invention

A preferred embodiment of the treatment method according to this invention is diagramed in FIG. 1. An initial laboratory test panel (box 1) is first run which would consist of the respective set of "disease markers" and the universal panel of "repair markers" consisting of signal transduction/second messenger panel molecules. Additionally certain laboratory assays are used to assure that the dosages are safe for the patient being treated. For defibrotide these may include prothrombin time, activated partial prothromboplastin time, thrombin time, reptilase time, bleeding time, platelet function assays and coagulation factors (see baseline coagulation panel). "Disease markers" are utilized to indicate the overall therapeutic efficacy of the doses. These markers may be identified through blood tests, urine tests, clinical observation or identification of blood clots by any of several conventional techniques, or by the more refined techniques such as DNA fingerprinting and PCR. To evaluate the "disease markers" the laboratory analyses measure levels of certain proteins, lymphokines, enzymes and relevant molecules. Clinical markers may include blood pressure, visible tissue damage, signs of inflammation, ecchymoses, and the like.

An initial bolus of defibrotide (box 2) is given intravenously over 15 to 30 minutes. Immediately thereafter the patient is given the daily dose of 40–400 mg/kg by continuous infusion. Preferably, the initial dose is a bolus (25–50 mg/kg) followed by 24-hour dose which is increased in 50 mg/kg/day increments every 1–3 days. The starting baseline dose may be from 40–400 mg/kg/day depending upon physician preference and the respective disease state treated. Lower initial doses are preferred for those therapeutic compounds which enter the cell nucleus more readily and are thus effective at lower doses. The bolus and daily dose for chemical derivatives of the nucleic acids may be calculated as a proportion of the defibrotide dose based on the relative cell-entry rate. It is preferred to administer this dose intravenously using two IV bags of 50 ml D5W, each bag infused over 12 hours. If for any reason the infusion is interrupted, the rate of infusion would be thereafter adjusted so that the patient will have received the calculated 12 hour dosage at the completion of the specified time period. This 24 hour dose range can also be administered in 2–4 bolus injections or per oral administration.

Defibrotide or other selected nucleic acid derivative may be administered parenterally, orally or locally by application to the skin. Parenteral administration is in the form of continuous intravenous infusion or intravenous bolus injection. Intravenous infusion may be accomplished by gravity feed, pump delivery or other clinically accepted methods. Oral administration may include the use of vials, capsules, tablets or powders for any method of enteric administration.

To permit clinically practicable administration of defibrotide in the amount necessary, materials for delivery of the agent optionally comprise 2×50 ml D5W IV bags each containing one-half of the calculated total 24 hour dose in milligrams of defibrotide, each bag infused over 12 hours for the IV-continuous infusion at the maximum tolerable doses. Alternatively, the total 24-hour dose can be administered by bolus injection every 8–12 hours. The initial bolus injection and the subsequent outpatient bolus maintenance infusions are given, for example, in 3×25 ml D5W bags, each bolus to be infused over fifteen to thirty minutes. The oral dosage outpatient maintenance therapy in milligrams given daily (divided into 3–6 doses by mouth) would be the multiples of 2X the maximum tolerable IV dose.

The same dose is given for three days and the laboratory test panel is repeated (box 3). A full coagulation profile and tests for markers should be run before and after any dose escalation. These tests results are compared with the initial test data to determine if any of the markers (which may include laboratory data or clinical observation for the disease being treated) have changed. A change is expected to occur in at least one marker within 3–21 days, indicating that defibrotide is having an effect. After each test the dose of defibrotide is increased by 50 mg/kg/day, dose for chemical derivatives being proportional to the cell entry rate for the respective nucleic acid, and continued at that dose for three days before retesting. This pattern of escalating the dose and repeating the laboratory panels is repeated (boxes 4 and 5) until the patient's "maximum tolerable dose" (MTD) is reached or until the disease/repair markers have plateaued or completely normalized.

If three consecutive values for a selected marker are about the same, a plateau has been reached. This procedure is followed for a minimum of 21 days (box 6). Disease/repair markers are checked and coagulation profiles are run on weekly intervals to monitor response. If no response is observed, i.e., no change in the level of any marker (box 7), therapy is discontinued (box 8), and treatment is determined to have failed. If, after 21 days (box 6), no plateau is reached, but improvement in the disease markers has occurred (box 14), the dose may be doubled or the MTD may be given (box 15).

If the markers are normal (box 9), therapy is discontinued (box 10). Tests continue to be repeated weekly for up to three months, noting any change in markers that would indicate relapse. If no relapse has occurred and no new markers have appeared after three months (box 11), therapy is discontinued (box 12) and the patient is considered cured. Should an old marker reappear or a new marker appear (box 13), the last previous dose is doubled, and therapy is resumed at that dose level. If doubling of the dose would exceed the MTD, the MTD would be administered.

Selection of Markers

The correct identification of markers are based on the identification of the pathways of disease pathogenesis and the respective repair processes and pathways. The mechanism of efficacy of the therapeutic nucleic acid simulate or are superimposed on the cellular pathways of the respective repair process they induce. For example, using defibrotide as the clinical agent, one would (1) identify the known signal transduction systems and second messengers of the repair process, (2) define the most probable nucleic acid-induced repair markers of the known cellular repair pathway, and (3) define markers of the disease process related to disease pathogenesis.

Many disease processes are pathogenically based on overactive body defense mechanisms. As such, a compound whose intracellular concentration can be a repair marker in one disease state can be a disease marker in another disease state. In such a case, the marker would usually be under-regulated by defibrotide instead of induced. Similarly, a marker of normal cellular function, if deficient, may be a disease marker. For example, the paralysis of cellular function of CD4 cells by the HIV retrovirus is secondary to the compromise of normal cellular markers of transduction pathways and second messengers.

G-proteins instrumental in the activation of adenylyl cyclase are likely to be deficient in their active form with a low dose threshold level. In this case, the deficiency of the normal cellular marker of G-proteins would be a disease marker. Since defibrotide affects the adenylate cyclase pathway (increased cAMP by defibrotide), defibrotide would restore the second messenger of cAMP, which therefore would be a repair marker.

The maximum therapeutic dose in turn would again follow the guidelines described above for vWAg, since this universal marker will get elevated with modulation of any phase of repair process such as, for example, receptor up-regulation, signal transduction or induction of translation and/or transcription, shutting off of transcription/translation which in turn may happen by activation of CREM, which is the inhibitor transcription factor of CREB, i.e., the latter is cAMP dependent initiator of the transcription factor of the CRE which in turn is the portion of the DNA enhancer sequence responsive to cAMP and cAMP associated transcription factors, such as c-myc products, c-fos products, ATP Activation Factor, Serum Responsive Element (SRE), API transcription factor (ATF), HIV-Long Terminal Repeat (LTR), leucine zipper transcription factors of c-fos/c-jun. (ATF, SRE, AP1 sites in c-fos promoter/enhancer all respond to cAMP without the requirement of SRE. Protein Kinase A activates endogenous CREB activity and will enhance viral transactivation).

The prototype high molecular weight defibrotide, native defibrotide, low molecular weight native defibrotide, and chemical defibrotide derivatives regulate genes which are regulated by cAMP. These genes include vasoactive intestinal peptide (VIP), somatostatin, human chorionic gonadotropin, phosphoenolpyruvate carboxylkinase, tyrosine hydroxylase, fibronectin, prolactin, ornithine decarboxylase, interleukin-6 gene, c-fos oncogene, haptoglobin, hemopexin, C-reactive protein (CRP), as well as other cellular genes which are regulated by cAMP responsive element (CRE), transcriptional factors interacting with CREB (which is 43 kd protein that interacts with CRE via leucine zipper, such as c-myc products, c-fos products, ATP (Activating Protein), SRE (serum responsive element), API.

Protein kinase A will activate endogenous CREB activity and will also enhance viral transactivation. CRE/CREB related transcription of genes including HIV Long Terminal Repeat (LTR) will be positively induced with high cAMP levels.

The selected nucleic acid, e.g., defibrotide, will affect only injury-dependent parameters in each individual patient. As such, no uniform action will be observable in all patients. For the nucleotide transcriptionally-activated parameters, analysis is made for the highest values in each dose range. For the nucleotide transcriptionally shut-off parameters, analysis is made for the lowest value in each dose range.

Therapy Based on Universal Markers

Several markers have now been shown to reflect transcriptional genomic activity by nucleotides which increase cAMP, adenylate cyclase via the interaction of G-proteins, and phosphorylate transcriptional factors via protein kinase A. Such markers include von Willebrandt antigen (vWAg), tissue plasminogen activator antigen (AgTPA) and $\beta_2$-microglobulin. While vWAg, AgTPA and $\beta_2$-microglobulin are representative markers, any molecules which are initiated by nucleotides, or derivatives such as defibrotide, to induce transcriptional activity are included.

It has been discovered that vWAg may be employed as a universal marker to guide the assessment of the duration of therapy, i.e., the most therapeutic dose, as well as the most efficacious daily dose. The inventors have discovered that vWAg is transcriptionally activated by defibrotide irrespective of the type of injury. Analysis of patient data has led to the unexpected finding that with the onset of cure, vWAg levels decline. The production of vWAg will be activated by defibrotide only for the duration of the injury and the repair process. In this regard, defibrotide will not effect vWAg levels in healthy individuals or following the establishment of cure, i.e., vWAg level will decline to baseline regardless of ongoing therapy. Concurrent analysis of vWAg with various "disease markers" correlated with changes in the disease marker levels. In other words, it has been discovered that therapy dependent absolute changes in disease markers (decline or increase) correlate with peak vWAg levels. The normalization of disease markers, in turn, correlates with decline in vWAg levels.

vWAg is classified according to this invention as being a universal dose marker. vWAg can be utilized as the universal marker for all nucleotides that induce activation of cAMP and protein kinase A enzymes. vWAg is a plasma glycoprotein having a molecular weight of approximately 200,000 which is constitutively secreted by the endothelial cell. It is important in hemostasis as a prothrombotic factor (factor VIII/vWAg protein) and as an inducer of adherence of platelets to the exposed subendothelium. In every disease state, vWAg levels go up with increasing defibrotide dose levels when the dose is adequate to stimulate vascular endothelial function.

In accordance with the invention, an increase in the vWAg level corresponds to the induction of transcriptional activity of this gene by the nucleic acid. Elevation of vWAg is representative of the ongoing repair process. The decline in the level and eventual normalization of vWAg during therapy is representative of the cure process. Plateau in the level of vWAg correlates with the application of the maximum efficacious dose. Without exception, the elevation in the level of vWAg is concurrent with modulation of the disease marker and activation of the repair marker. Here the maximum efficacious dose is determined along with vWAg, so as to normalize the levels of these molecules between 65–150%, and eliminate the intracellular oxygen radicals (measured by chemiluminescence, normal state being negative). For the prototype drug, defibrotide, the maximum efficacy in inducing transcriptional activation of vWAg occurs at doses of 40 DKGD and above, ideally within the DKGD range of 40–400. The universal marker vWAg dose levels are representative dose levels by the prototype's transcriptional/translational modulatory effects. Fitting the definition of universal marker, vWAg does not contribute to the expected correction of bleeding time but acts as a functionally dormant molecule.

Another option is to empirically repeat therapy after three weeks following cessation of therapy on the above principles. In this regard, the half life of the nucleic acid appears to be about three weeks, based on the observation that universal marker vWAg requires 2–3 weeks to come down to baseline levels with cessation of therapy. If the universal marker vWAg is elevated during therapy with the previous maximum efficacious dose, there is still a lesion to treat, irrespective of the fact that there are no known or visible clinical, and/or documented biochemical repair or disease markers.

Therapy, in accordance with the invention, is geared to continue until vWAg is normalized while on established maximum effective dose. Thereafter therapy is discontinued and the same cycles are repeated until the maximum efficacious dose therapeutically initiated no longer induces any elevation in vWAg, as would be observed in a normal healthy individual.

Statistical Analysis

A statistical model has been used to assess the dose and duration of therapy with the ultimate objective of irreversible cure. For each molecular marker, calculations are presented, based on analysis of the data from all the patients for the "first day value," the "last day value," the "highest value" or "lowest value" (i.e., for transcriptionally activated molecular markers and for transcriptionally inhibited molecular markers, respectively), the "m-efficiency score," and the "time required to reach the optimal effect of the nucleotide" at the dose ranges employed. The "first day value" at a particular dose is the "last day value" of the preceding dose range. The "minimum of increasing values" has been found to be the best parameter to follow for transcriptionally turned on molecules while the "maximum of the lowest values" has been found to be the best parameter to follow for transcriptionally turned off molecules.

The best parameter to follow the dose related induction of transcriptional activity is the "minimum values of the increasing levels" obtained on the first day of the initiation of each dose range. "Highest or increasing levels" represent the increase in level of a molecule whose production (transcription) is turned on with increasing dose levels. Choosing the minimum increase in the level in the transcribed genome among all patients treated in any dose range enables the prediction of the worst performance with that dose of the therapeutic compound. This enables the treatment of the worst performer, which allows turning on the genomic transcriptional activity in the greatest number of patients within each respective dose range. Increase in the marker, as shown by "minimum highest value" represents that the repair process is ongoing, that is, repair molecules are being produced and transcriptional activity is ongoing.

The quantitative relationship between vWAg level and daily dose of the therapeutic compound is best visualized when the minimum value of the increasing vWAg levels in the population are analyzed (i.e., the worst performance levels in any one patient at any one dose range, "worst performance" implying that increasing the dose will incrementally continue to elevate the vWAg, which is biologically interpreted as meaning that there are more repair events to go through).

Minimum increasing value is the parameter to use to confirm the event of ongoing cellular repair. Maximum increasing value is the statistical parameter to use to follow the completion of the repair event. Maximum therapeutic dose is the dose at which vWAg on continued therapy will decline to a normal level.

The "maximum values of the lowest levels" obtained among all patient data on the last days of treatment at each dose range are similarly used to analyze how increasing dose ranges affect the transcriptional activities involving the "turned on" molecules. The levels will show progressive declines, i.e. , the progressive turning off of the repair process with the onset of cure, in spite of the higher doses.

Once maximum stimulation takes place (as assessed by the use of first day minimum highest levels), the cell gets turned off. By the use of the maximum lowest levels of the last day, therapy is continued at that particular dose level until these levels return to the baseline levels on therapy, i.e., until there is no more ongoing transcriptional activity, i.e., the repair process is completed.

The m-efficiency value is the ratio of the respective elevated level over the time taken for elevation to occur. The higher the dose, the higher the value of the numerator and the higher the m-efficiency level. Alternatively, the shorter the time (denominator), the higher is the m-efficiency value.

Method of Treating HIV-Infected Patients with Defibrotide

Defibrotide's mechanism of efficacy relates to modulation of cell functions at the nuclear genomic level through one or more pathways by modulation of the cell's genetic material, i.e., DNA itself or translation or transcription of the genetic information. Defibrotide-induced cellular modulation restores the normal functions of the cell such as the production of normal proteins needed by the cell and, in the case of HIV, the correction of the effects of the abnormal, viral encoded genetic material by inhibiting its further production at the expense of the normal, virus-free genetic material. In the course of the multi-phase treatment, defibrotide is administered at dosages much greater than previously described in the literature for other disease states. The dosages and durations of the phases of therapy are adjusted according to the results of laboratory studies performed on the patient's infected cells. Preferably, in treating HIV, an initial bolus dose of 100 mg/kg in 50 ml DSW is infused over a period of 30–60 minutes followed by 200 mg/kg/day infused in 250–500 ml DSW over a period of 3–24 hours. From day 2, dose is escalated to maximum tolerable dose, maximum efficacious dose and maximum therapeutic dose levels. In this way, the HIV virus may be inactivated and its proliferation arrested. Therefore, the progress of the disease may be arrested or ameliorated.

Because HIV virus adversely affects the genetic material and function of the cells, defibrotide can effectively treat HIV infection as long as the carrier $CD4^+$ cell and/or the monocyte harboring the virus preserves the physiological ability to revive itself. Therapeutic success with defibrotide, however, is strictly dependent upon the assessment of the correct treatment doses for the respective disease states. Moreover, since the optimum function of the normal cell, by definition, would not be compatible with any complications, defibrotide at any defined maximum efficacious dose, specific for any patient and disease state would be complication-free.

Sarin et al. (*Proc. Natl. Acad. Sci. U.S.A.*, 1988, 85: 7448–7451), as well as Leonetti et al. (*Bioconjugate Chem.*, 1990, 1: 149–153), have shown that antisense oligonucleotides are potent inhibitors of HIV-1 replication in cell culture. The methylphosphonate linked oligonucleotides were found to be superior in this effect over the phosphodiester linked oligonucleotides, apparently as a result of their resistance to nucleases. This property was deemed to be the factor in the superiority, since oligonucleotides less than 20 bases in length proved to be ineffective inhibitors.

Efficacy of defibrotide may have several concurrently active mechanisms. Defibrotide may provide anti-sense neutralization of the viral proteins. Defibrotide's mechanism of efficacy may be at the nuclear level by modulation of genetic functions via other pathways as well. Defibrotide's actions may be more apparent during viral phases which involve translation and/or transcription of the DNA message, so as to revive the normal function of the cell at the expense of the disease-specific molecules. This action may be analogous to anti-viral effects of Ampligen (a mismatched double stranded RNA-molecule). However, whereas Ampligen exhibits immunostimulating effects, agents such as defibrotide are both immunostimulants and immunosuppressants. Defibrotide may modulate viral penetration into the cell via its known action of inhibiting intracellular calcium mobilization. Also, defibrotide may directly inhibit viral enzyme reverse transcriptase via inducing ATP production analogous to ddI (dedeoxyinosine), by virtue of its known action of inducing high energy metabolites (ATP, ADP, NADP/NADPH), possibly via modulation of Complex-I respiratory molecule. Defibrotide may inhibit protein kinase C, analogous to Hypericin. Defibrotide may also decrease Tissue Necrosis Factor (TNF), a cytokine known to promote HIV activation, by its known effect on increasing cAMP levels at the correct defibrotide dose level similar to Pentoxyfilline.

Whatever the mechanism, zinc is known to have an inhibitory effect upon nucleases acting on phosphodiester linkages, as well as an enhancing effect on base pairing. U.S. Pat. No. 3,770,720, teaches that in the production of defibrotide, zinc should be removed from the molecule. However, in the treatment of AIDS, it is preferred that zinc be present. Moreover, it is preferred that iodine should also be present. In the defibrotide used in the Examples iodine was present in an approximate ratio of one zinc atom per iodine atom and a two to one ratio of zinc + iodine to nucleotide base.

As can be seen from comparing the cellular uptake data shown in FIGS. 2 and 3 with the data shown in FIGS. 4, 5 and 6, a greater level of defibrotide enters the lymphocytes when biotin is present. Horn et al. (*Plant Physiol*, 1990, 93: 1492–1496) has observed that biotinylated molecules enter the cell via the folate endocytic pathway. The data of FIGS. 2–6 read in conjunction with the above-cited Horn reference, indicate that defibrotide with biotin may also use the folate endocytic pathway.

Defibrotide may jointly and/or selectively modulate one or several pathways. This modulation will be, only to the appropriate degree thus surpassing all of the other anti-HIV agents in its lack of side effects, yet presence of proven efficacy. Defibrotide will achieve this result only when the dose levels are tailored to the patient, stage of disease activity and/or reigning stage of viral activity.

The method of treating the HIV-infected patient begins with a panel of laboratory studies which include the quantitative evaluation of the activated peripheral blood mononuclear cell subsets, circulating viral proteins, cytokinases and soluble cell-surface receptors. There are no patient inclusion or exclusion criteria for therapy. Patients in any or all of the four clinical stages of HIV-infection including history of exposure (i.e., HIV$^+$, Pre-ARC, ARC, and AIDS) are candidates for therapy. The initial administration of a selected dosage of defibrotide is followed by incrementally increasing the dosage of defibrotide until a maximum tolerable dose is reached. The laboratory panel is repeated weekly during this therapy. These results together with the clinical markers of disease would indicate whether the defibrotide is efficacious and whether defibrotide should be continued to be given alone or with other therapeutic agents.

The details of treatment and the dose ranges fitting the various stages of the HIV disease will be expressed by retrospective analysis of respective laboratory and clinical markers. Additionally, dosage levels and frequencies as well as the use of other anti-HIV medication will also depend upon the individual patient or stage of disease and/or other concurrent medical conditions.

Before the initiation of therapy and weekly thereafter blood is drawn from the patient and subjected to a panel of tests which preferably include activated peripheral blood mononuclear cell subsets by two-color flow cytometry, lymphokines and soluble cell surface receptors by ELISA, and HIV-viral proteins by Western blot analysis. The peripheral blood mononuclear cell subset analysis will usually include either CD4$^+$, CD8$^+$, CD19$^+$, CD25$^+$, CD56$^+$, and HLA-DR alone, combined with one another, or combined with the quantification of monocytes. The Western blot protein tests include gp-24, gp-17, gp-120 and gp-160. The ELISA test measures TNF, sIL2R, sIL1 and soluble CD8. Every third week, it is preferred that cell cultures for HIV antibody neutralization, PCR and reverse transcriptase determinations be made.

HIV-I Gene Therapy in Accordance with the Invention

Gene delivery thus far has been a method by which foreign genetic material is introduced into a suitable target cell usually via viral vectors. Such strategy generally consisted of an ex vivo and an in vivo phase. In the ex vivo phase the foreign gene is inserted into target cells derived from the recipient. The engineered cells containing the newly inserted gene are expanded ex vivo. In the in vivo phase, the expanded engineered cells are transplanted into the recipient.

This modulatory therapy is the first of its kind which manages therapy from cell surface signaling to genomic modulation utilizing the oral and/or intravenous administration of nucleotides, without utilizing retrovirus, adenovirus or other gene viral vectors traditionally employed in gene therapy. Gene therapy has not, heretofore, been utilized without cellular transfection with viral vectors, and never before by oral or intravenous administration of nucleotides to humans.

Gene therapy has not, heretofore, been tried without the interaction of viral vectors, i.e., by the administration of nucleic acid-based pharmaceutical agents orally and/or by intravenous route. The prototype drug defibrotide, although administered to patients over the past 5–6 years, has never heretofore been contemplated for gene therapy. In addition, in other modalities of gene therapy, dosage has never been assessed by molecule markers. Molecule markers have never been defined within the system of secondary messengers, signal transduction systems, promoters (DNA sites which are on the same chromosome as the gene transcribed and to which RNA polymerase binds), enhancers (DNA regions that control a promotor from a great distance, sometimes as much as 30,000 bases), and transcription factors (diffusible regulatory proteins which bind to DNA transcription activation domains and regulate the rate of transcription by RNA polymerase).

HIV-disease has not been previously interpreted as a disease of dismodulation involving the genomes, cellular secondary messengers and cellular signal transduction systems. The specific pathways affected by the HIV-retrovirus have not been clearly delineated. Therapy of HIV-disease has not previously attempted to reclaim the affected cellular function systems from the virus by reversing the dismodulation at the various levels by using exogenous therapy involving various modulators of these systems.

The therapeutic approach of the invention disengages itself from the common practice of planning therapy based on clinical staging. The planning of therapy is based on the identified mismodulations of (a) membrane lipids and cytoskeleton; (b) cell-surface receptor/ligand interactions; (c) secondary messengers; (d) signal transducers; (e) cellular transcription factors utilized in viral replication: as well as based on the identified (f) oncogenes; (g) viral transcription factors; and (h) viral genomes. The method of therapy disclosed herein for HIV may also be used in treatment of other viral infections and neoplasms.

These mismodulations are classified into marker categories of (i) repair markers (items a–e) and (ii) disease markers (item f–h). The object of therapy in accordance with the invention is to (i) reestablish repair markers at the constitutively expressed tissue levels; and (ii) eliminate disease markers (in case of the oncogenes to reverse the transformation).

Irrespective of disease stage or clinical status the patient is screened with the complete panel of secondary messengers and signal transducers (repair markers), since all repair markers are biochemically interdependent. Repair markers reflect the underlying logic of transcriptional regulation. Therapy is aimed to concurrently induce some markers and suppress other markers. The prototype nucleotide if used at the correct doses (which are guided by the respective repair markers) can accomplish this goal.

Elimination of disease markers by the therapeutic nucleotide compound will occur at various levels. It can be an indirect phenomenon based on modulations of secondary messengers, such as cAMP; it can be a direct phenomenon based on modulations of the phosphorylation events involving genes and transcription factors. For example, cAMP activates protein kinase A enzymes, Ca$^{2+}$ activates protein kinase C enzymes, the prototype nucleotide up-regulates cAMP, and downregulates Ca$^{2+}$, or it can be a direct phenomenon based on modulation of cAMP responsive gene promoters (CREM, as enumerated above).

While not being bound to any specific mechanism of action, the following are proposed.

Proposed Mechanism A.

Induction of sIL2R gene and HIV-I LTR are interdependent phenomena. If the protein kinase C dependent sIL2R gene is turned off by high cAMP levels, activation of HIV-I LTR is concurrently suppressed as well.

Proposed Mechanism B.

Increased cAMP levels have been shown to induce viral replication (Nokta and Pollard, 1992, *AIDS Research and Human Retroviruses* 8(7): 1255–1261). HIV-I REV/ENV genes are both phosphoproteins. There may be other routes for cAMP-induced replication of HIV-I. Although administration of the maximum efficacious dose will increase cAMP levels, prolonged administration of the nucleic acid at the maximum efficacious dose, so as to realize the successful administration of the maximum therapeutic dose would culminate in declining cAMP levels, since vWAg decreases on therapy if and once the maximum therapeutic dose is administered. Hence administration of the maximum therapeutic dose is paramount in overcoming cAMP induced viral replication. This phenomenon may at least partially, be based on the induction of protein kinase C, as a secondary biochemical event (i.e., protein kinase C induces sILR2 gene, which in turn modulates protein kinase C so as it can directly inhibit cAMP).

Proposed Mechanism C.

The transcription factor NF-kB binds to both the HIV-I enhancer, and the sILR2 gene. Protein kinase C phosphorylates its inhibitor IkB and releases active NF-kB. Increased cAMP levels by inhibiting directly the $Ca^{2+}$ induced activation of protein kinase C would modulate this phosphorylation event, and downregulate the transcriptional activities related to NF-kB. Since NFkB binds to both the HIV enhancer and IL2 receptor, increased cAMP levels will downregulate HIV-I replication.

Proposed mechanisms B and C show that increased cAMP levels can be both deleterious and beneficial. It can be clearly seen that the prototype nucleotide is an overall "downregulator" of biochemical events, if maximum therapeutic and efficacious dose levels are administered.

It has also been discovered that the co-administration of various sequence specific, anti-sense or missense nucleic acids with, for example, defibrotide, would (1) alleviate the complication of cAMP induced viral replication; (2) induce inhibition of viral replication mediated via modulations of cAMP, protein kinase A, protein kinase C, cellular redox state, G-proteins, or cAMP induced gene promoters (in this regard, defibrotide and other nucleotide derivatives introduce for the first time into anti-HIV therapy nucleotides with no sequence specificity that concurrently modulate the totality of the cellular second messenger/signal systems for rapidly transducing extracellular signals into specific patterns of gene expression in the nucleus); (3) concurrently induce inhibition of viral replication with sense, anti-sense, or missense nucleic acids (e.g., DNA, mRNA, DNA/RNA ribosomes, inhibitors of viral protease, viral integrase); and (4) introduce a modality of gene therapy (i.e., genetic engineering) which can be safely administered to humans, which does not utilize viral vectors, which can be administered either intravenously or orally, which enables administration of sequence specific combination of nucleic acids adjusted specifically to the selected parts of the HIV-genome and cellular repair pathways, which adjust the dose so as to modulate selected genes or cellular/viral molecules, which enables the most efficient administration of various different nucleotides with differing cellular uptake dynamics and chemical anti-viral potencies, and which administers excess DNA to enable the self-integration of DNA.

This process is superior to present viral vector directed gene therapy and would also enable competitive inhibition of proviral integration, and/or dislocation of the integrated pro-virus. Cellular uptake dynamics would directly define the anti-viral and genetic modulatory capacities of each respective nucleotide. Nucleic acid derivatives having chemical modifications are as described previously (e.g., nucleotides conjugated with poly(L-lysine) or which is modified by, for example, the addition of amino acids such as lysine, histidine and arginine, the addition of optimum concentrations of folate and/or biotin, the addition of the optimum ratios of metals and ions including zinc, manganese and iodine, by the addition of 5'-polyalkyl moieties, cholesterol, vitamin E, 1-2-di-O-hexadecyl-3-glyceryl and other lipophilic moieties and/or modified by the replacement of phosphodiester bonds with phosphothiotate bonds) and combination nucleic acids would be employed.

Combination nucleic acids will, hereinafter, be referred to as "combo-nucleic acids". Combination of sequence non-specific prototype nucleic acids (e.g., defibrotide and derivatives thereof) with various sequence specific nucleotides has never, heretofore, been proposed for use as a multimodal therapy for HIV.

Various sequence specific nucleotides, such as TAR decoy RNA, negative mutants of the viral REV transactivator, synthetic promoters with the consensus sequence for binding of the transcription factor Sp1, and the TATA box, TAT mutants, mutations involving the seven cysteine residues, REV mutants, NEF-cDNA sequence with or without U3 region sequence of the 3'LTR, HIV-I LTR enhancer (−137 to −17) mutant, HIV-I LTR sense sequence of the negative regulatory element (−340 to −185), LTR Sp1 (GC box) binding site and TATA box mutants and LTR GAG gene sequence mutants, are known in the prior art. However, such sequence specific nucleotides have been used only in the in vitro setting as "single mode" anti-viral agents, the mode of actions being limited to the sequences.

Examples of combo-nucleic acids are listed below:

a) defibrotide sequence+TAR decoy RNA, b) defibrotide sequence+negative mutants of the viral REV transactivator, c) defibrotide sequence+synthetic promoters with the consensus sequence for binding of the transcription factor Sp1, and the TATA box, d) defibrotide sequence+TAT mutants, mutations involving the seven cysteine residues, e) defibrotide sequence+sense derivatives of CIS acting negative elements (CRS) present in the integrase gene+ REV mutants, f) defibrotide sequence+transdominant suppressor of REV (mutations involving amino acid 78 and 79), g) de fibrotide sequence+NEF-cD NA sequence with or without U3 region sequence of the 3'LTR, h) defibrotide sequence+POL reverse transcriptase gene mutants, i) defibrotide sequence+POL viral integrase gene mutant, j) defibrotide sequence+POL viral protease gene mutant, k) defibrotide sequence+HIV-I LTR enhancer (−137 to −17) mutant, l) defibrotide sequence+HIV-I LTR sense sequence of the negative regulatory element (−340 to −185), m) defibrotide sequence+LTR NFkB mutant (−104 to −80), n) defibrotide sequence+LTR Sp1 (GC box) binding site and TATA box mutants, o) defibrotide sequence+LTR GAG gene sequence mutants, p) defibrotide sequence+ENV, GAG, POL gene sequences placed 3' of the REV mutant codon, and q) defibrotide sequence+host DNA sequence of preferred targets for proviral integration.

The sequence nonspecific chemical derivative in the combo-nucleic acids exemplified above are preferably also modified for improved cellular uptake, and enhanced anti-viral activity with the chemical modifications described above.

EXAMPLES

Example 1

Figure 2:
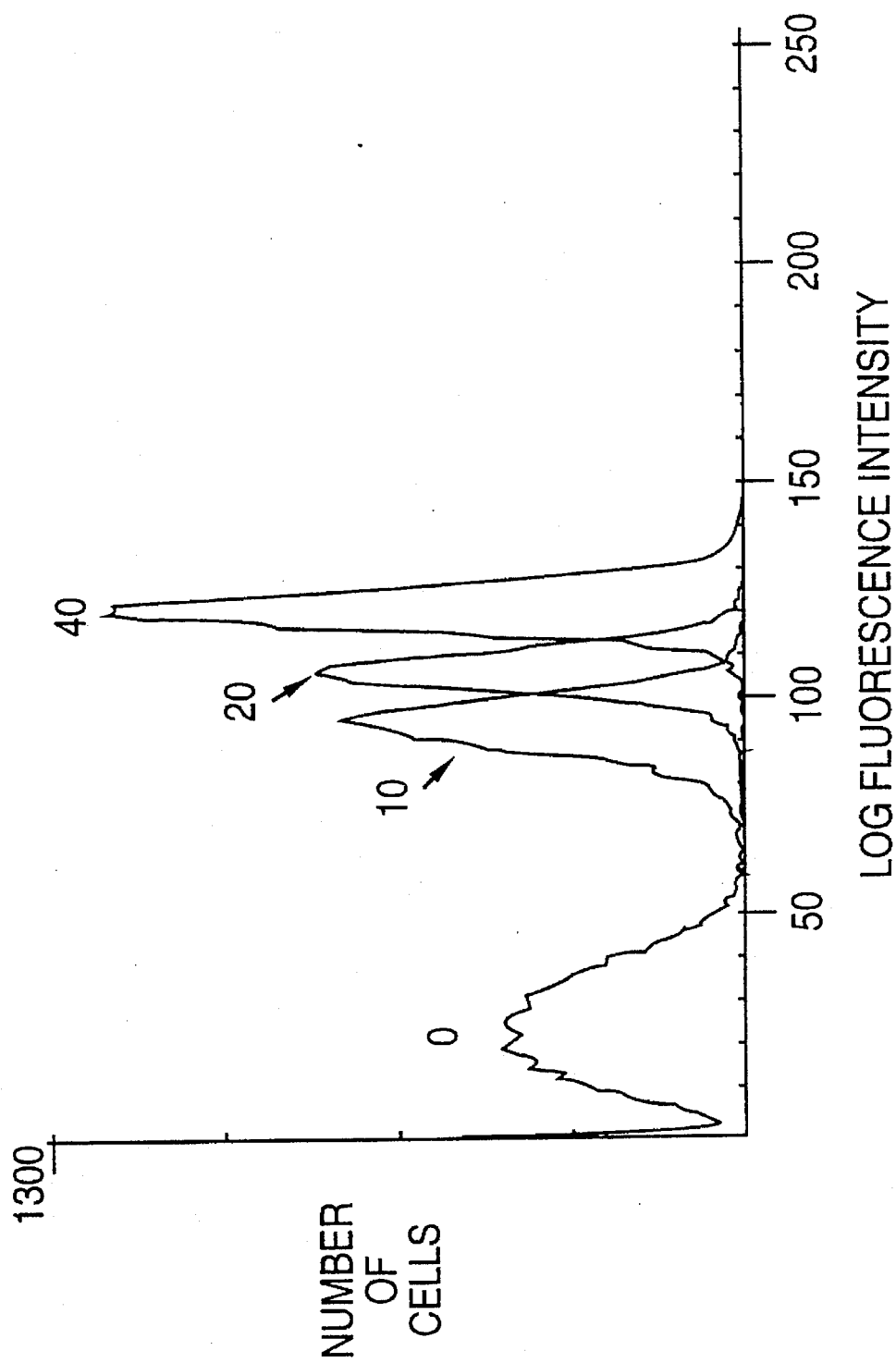
FIG. 2 is a graph showing normal peripheral blood cells labelled with 0, 10, 20 and 40 µg defibrotide-biotin combination.
Figure 3:
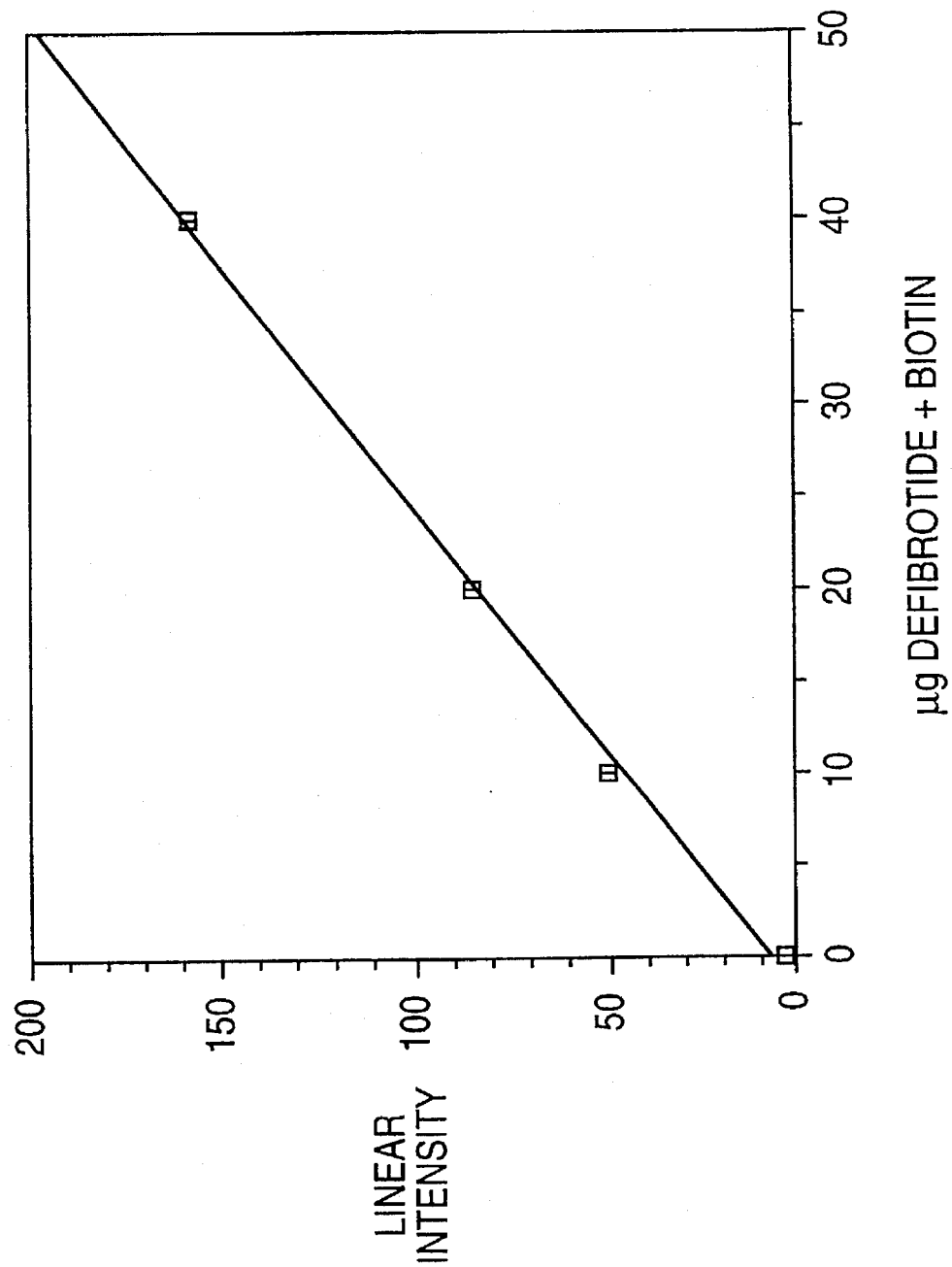
FIG. 3 shows the data of FIG. 18 on a linear scale.

To measure the effect of defibrotide on HIV it was first necessary to label the drug and determine whether defibrotide will enter the nucleus of the human cell. Knowing the phosphodiester linkages in defibrotide, its comparative nuclear penetration was assessed by labelling defibrotide with a photo-activatable analogue of biotin. The biological activity of defibrotide after labelling was considered to have been preserved since published data shows that previous oligonucleotide probes have been labelled with conjugates and still remained biologically active. Image analysis utilizing a cold CCD camera revealed that uptake of defibrotide was localized in the nucleus. This supports the hypothesis that the mechanism of efficacy for defibrotide is largely contributed to by its modulatory activity on the genetic material of the cell, no matter what disease entity is being treated. As shown in FIGS. 2 and 3, the nuclear uptake of defibrotide is directly proportional to the concentration of defibrotide with biotin. The observed uptake supported the increased efficacy of defibrotide with the larger doses used, and also supports the hypothesis that at critically high dose levels various previously unknown different effects of defibrotide can be seen. It was also observed that uptake by monocytes was significantly greater than that by lymphocytes.

Figure 4:
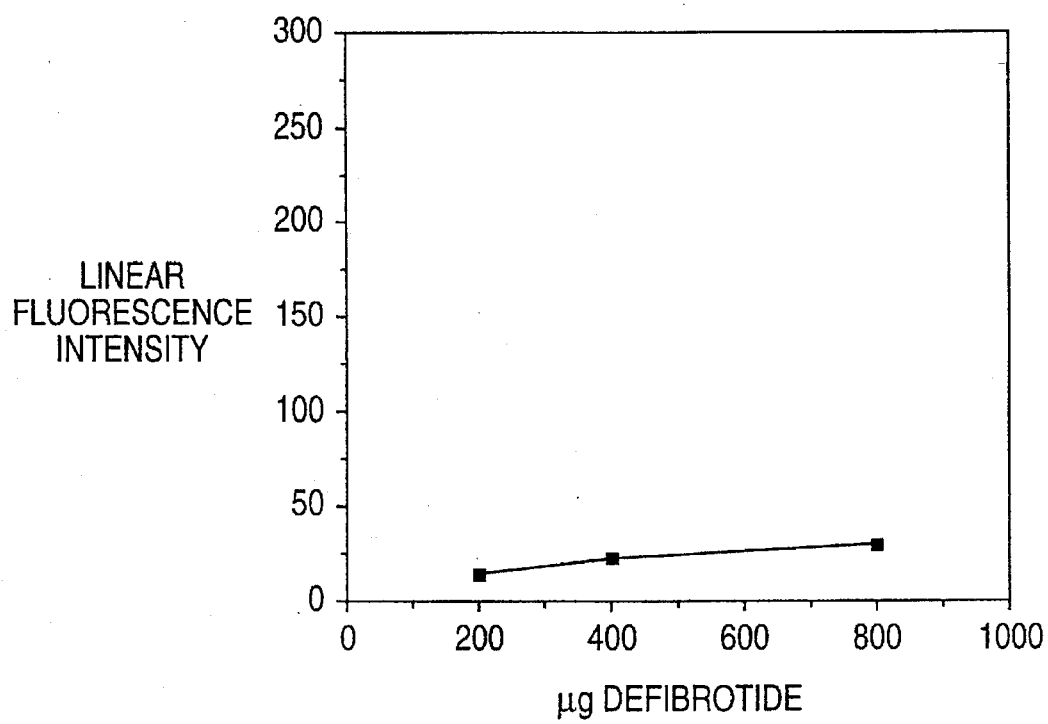
FIG. 4 is a graph showing the lymphocyte uptake of defibrotide without biotin and labelled with Cy5.18.
Figure 5:
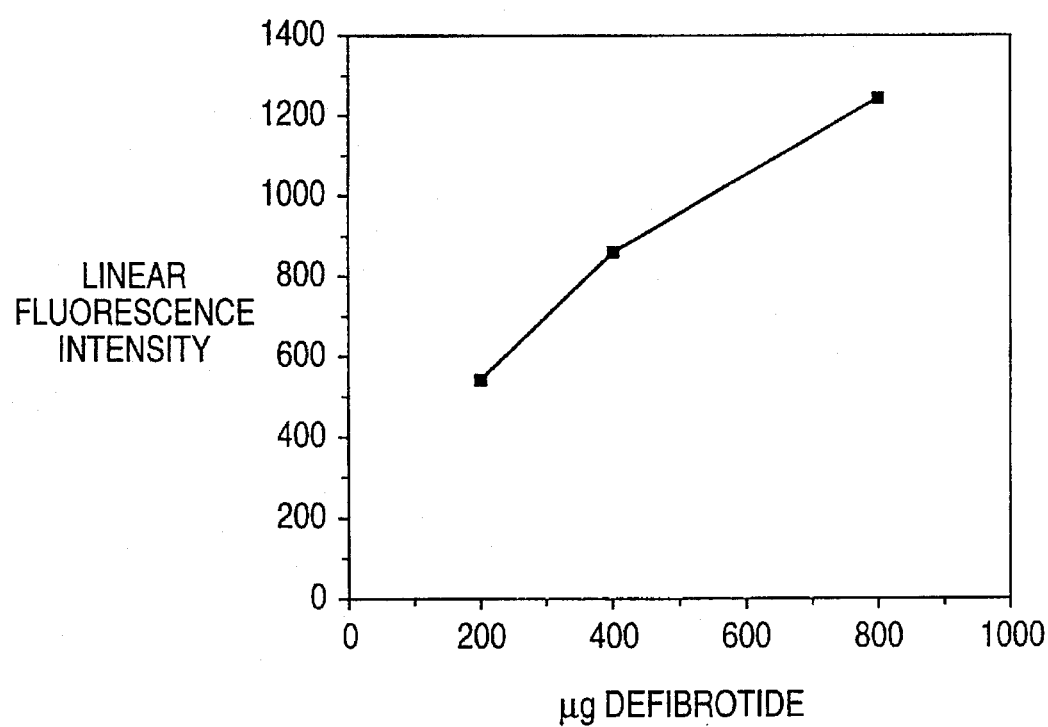
FIG. 5 is a graph showing the monocyte uptake of defibrotide without biotin and labelled with Cy5.18.
Figure 6:
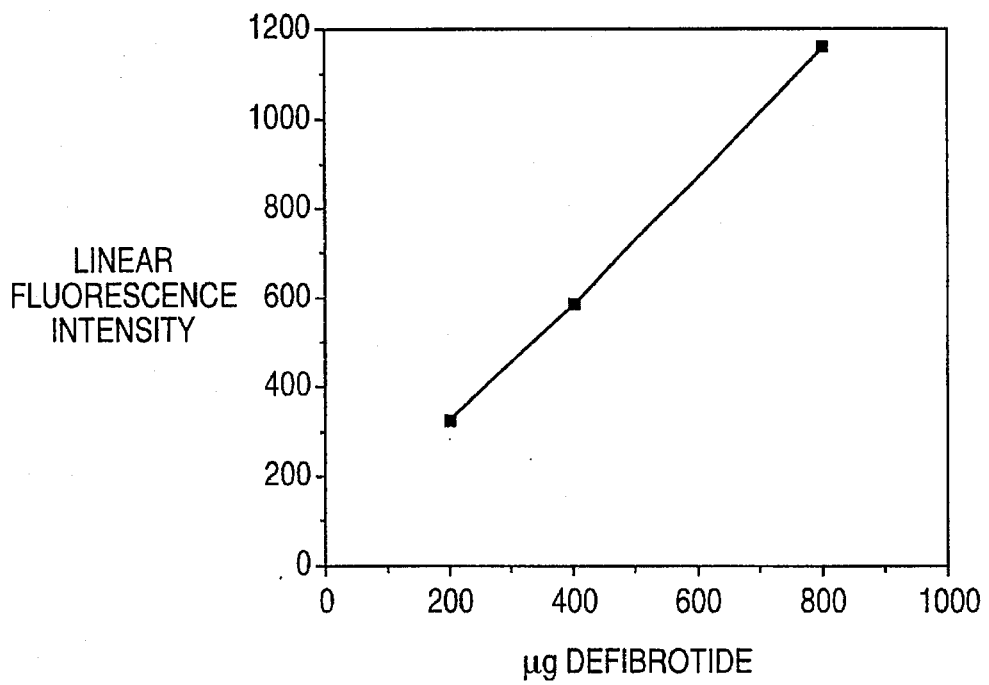
FIG. 6 is a graph showing the granulocyte uptake of defibrotide without biotin and labelled with Cy5.18.

The cellular uptake of defibrotide without biotin and labelled with cyanine dye Cy5.18 was also measured. It was observed that biotinylation of defibrotide enhanced the cellular uptake of defibrotide in the lymphocyte population. However, there was no difference in uptake between monocytes incubated with biotinylated or fluorescently tagged defibrotide. This can be seen by comparing FIGS. 4 and 5.

Example 2

To further confirm the specificity of defibrotide for the treatment of HIV infection, HIV infected peripheral blood mononuclear cells with varying doses of defibrotide were evaluated by staining for all viral envelope proteins using concanavalin A (Con-A) stimulated and unstimulated cells (Anti-HIV 1, and Anti-HIV 3 specific Anti-HIV antibody). The blood sample was obtained from a patient using an evacuated blood collection tube containing sufficient EDTA to prevent coagulation of the sample.

Mononuclear leukocytes (white cells) were obtained by layering a 1:1 (volume:volume) blood to RPMI 1640 tissue culture medium (Grand Island Biological Co.) aliquot over histopaque (d=1.077, Sigma Chemical Co.) under sterile conditions. The white cell population was suspended in a solution of the RPMI 1640 medium supplemented with 10% heat-inactivated fetal calf serum and gentamicin, at the concentration of 5 micrograms/milliliter. The white cells were then concentrated to a level of two million cells per three milliliters ($2\times10^6$ cells/3 ml) of the above solution. The white cells were collected in flat-bottomed microtiter containers (Cell Wells, Coening).

The cell populations were further divided into two groups. One group received stimulation by Con-A, the other group remained unstimulated by Con-A. Con-A stimulation enhances the uptake of the antibody-dye label by HIV-contaminated cell components, thereby demonstrating an increase in the expression of the HIV protein.

Subpopulations of unstimulated and stimulated white cells were then incubated in the presence of discrete concentrations of defibrotide. Each successive assay employed successively greater concentrations. A control sample of incubate containing no defibrotide was also prepared. A labelling antibody solution was prepared by directly conjugating Cy5.18 with human α-HIV antibody to a final dye/protein ratio of 5.0 (α-HIV-Cy5.18).

The cell subpopulations were again divided into two groups, one group for intracellular antibody labelling, and one group for surface antibody labelling. Cells reserved for intracellular labelling were fixed with 70% ETOH, washed twice with monoclonal wash, and then resuspended into a solution containing 200 microliters of Hank's balanced salt solution (HBSS), supplemented with 2% FCS and 0.1% sodium azide (monoclonal wash) and 5 microliters of α-HIV-Cy5.18 solution. The entire cell preparation was incubated for 45 minutes at 4° C. The cell preparation was then washed twice with the monoclonal wash, and resuspended in 1% paraformaldehyde.

Cells reserved for surface labelling were prepared by washing twice in monoclonal wash to which 5 microliters of α-HIV-Cy5.18 have been added. Next, 20 microliters of specific surface glycoprotein monoclonal antibody was added to the incubation solution. The surface glycoprotein antibody solution contained CD3FITC (heterogenous T-cell antibody conjugated with fluorescein isothiocyanate dye) and CD4-RPE (helper T-cell antibody conjugated with phycoerythrin dye) obtained from Becton-Dickinson.

All cells thus prepared were then analyzed using a Becton-Dickinson FACS 440 dual laser (argon/krypton) flow cytometer. The expression of HIV proteins was determined on a per-cell basis. Fluorescence was measured on a logarithmic scale but converted to a linear scale for analysis.

Figure 7:
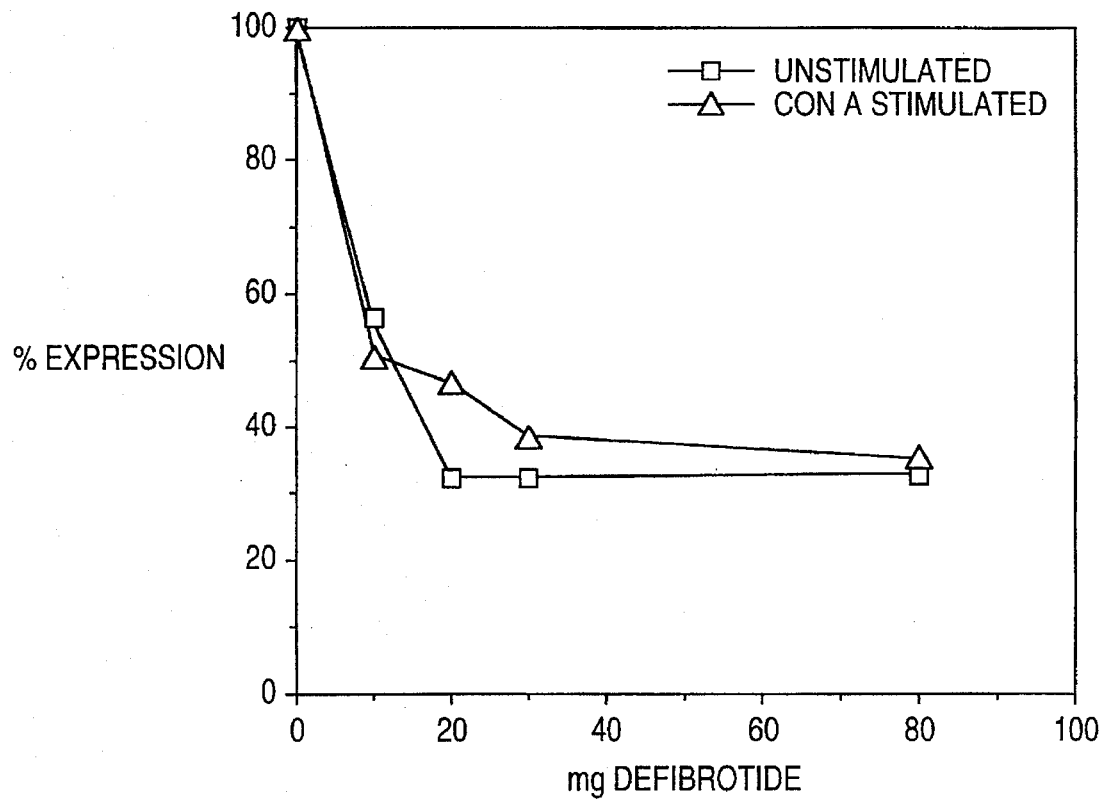
FIG. 7 is a graph showing the percent expression of HIV viral proteins remaining when blood lymphocytes of an HIV infected individual were exposed to various doses of defibrotide with and without Con-A stimulation.
Figure 8:
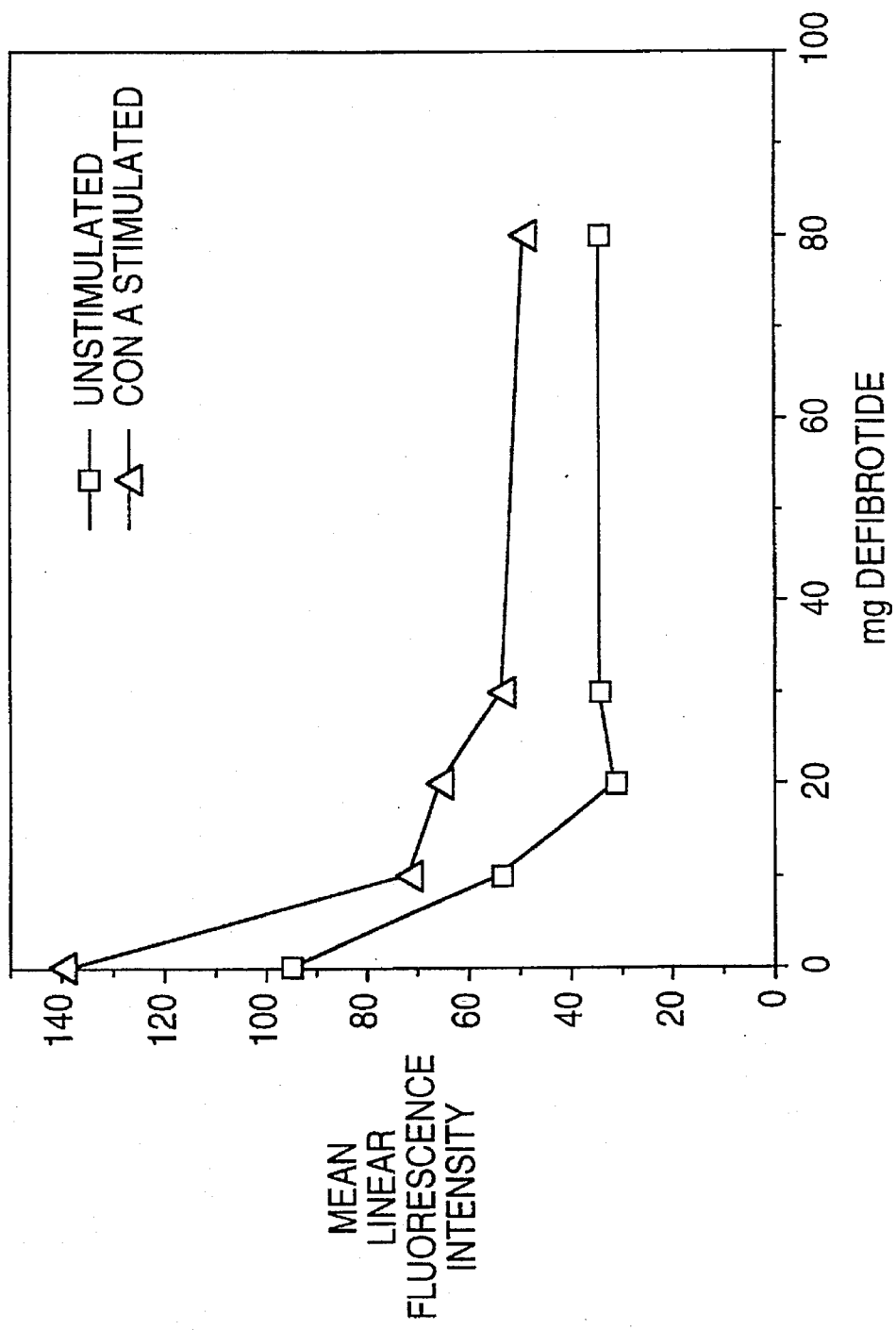
FIG. 8 is a graph showing the laboratory response expressed in terms of mean linear fluorescence intensity of the peripheral blood mononuclear cells of an HIV infected individual, the cells being subjected in vitro to varying levels of defibrotide using a cell culture assay technique with and without Con-A stimulation.

FIG. 7 shows HIV protein expression at selected dosages. Assay results for the same sample shown in FIG. 8 are in terms of the intensity of the fluorescence of certain antibody-labelled mononuclear leukocytes (Mean Linear Fluorescence Intensity). Fluorescence intensity is proportional to HIV protein expression, and thus the activity of HIV. It is seen that the expression of the HIV proteins decreases and then levels off with increasing concentrations of defibrotide.

Before administration of defibrotide, Con-A stimulated cells expressed 32% more viral proteins. However, after administration of 20 mg of defibrotide, both stimulated and unstimulated cells express 70% less viral proteins. At 30 mg concentration of defibrotide in both Con-A stimulated and unstimulated cells the expression of viral proteins leveled off. This supports the specificity of defibrotide for HIV-virus as well as the fact that if cells are induced to divide, translating into proliferation of the virus, more HIV virus can be killed, albeit, at higher doses.

Example 3

Patients with various diseases of vascular prothrombotic backgrounds were treated with escalating dose levels of defibrotide. A variety of coagulation and hematological assays with other molecular markers of inflammation, etc., were conducted on blood samples drawn from the patient before and after each dose escalation. From an analysis of the test results and clinical observations, it was discovered that certain effects of defibrotide lead to a remission state of certain specific aspects of disease states corresponding to the various dose ranges employed.

As an example, hematological recovery in thrombotic microangiopathy, generally, yet not exclusively, occurred when the patient received doses of defibrotide ranging from 20 to 30 mg/kg/day. These doses however did not cure the renal lesions since creatinine levels remained above normal (or only partially corrected) at the dose levels where hematological recovery was complete. Renal recovery evidenced by normalization of creatinine levels occurred between 40 and 250 mg/kg/day.

Even in the presence of normalization of creatinine levels (the conventional criteria of complete recovery) it was observed that complete remission was yet to be reached by the observation of elevation of blood pressure, low AgTPA and high fPAI levels. Therefore, doses of defibrotide continued to be increased until blood pressure levels became normal. The dose elevation not only treated blood pressure, but also led to further improvement of creatinine. Thus, treatment with marker-dependent doses, applied correctly, led to a state of "cure".

Example 4

In a normal individual, increasing the DKGD dose does not induce any elevation in the vWAg since there is no ongoing repair process, i.e., no disease state. Doses administered to a normal individual, in contrast to the doses given to an individual exhibiting a pathological disease state, did not induce any alteration in vWAg levels, i.e., defibrotide did not induce transcriptional activity at the genomic level. vWAg predicts the transcriptional rate of the respective repair molecules induced by the nucleotide and will guide the assessment of maximum efficacious dose and maximum therapeutic dose.

In a diseased individual, an increase in DKGD increases the preceding minimum highest value of vWAg by an increment smaller in each successive interval. Using defibrotide, the highest percentages of increments were found to occur at the borderline of 40 DKGD. Increasing DKGD above 400 induces only negligible improvements over levels below this dose. In practice, this is the dose level above which complications of bleeding have been observed by the inventor with high molecular weight defibrotide.

Examples 5–7

Examples 5–7 report the treatment of three HIV infected patients. This patients were all treated in Turkey with defibrotide obtained from CRINOS. In Tables I–IV, below, the following are the normal laboratory ranges: IL-1=3.6 pg; IL-2=4.3–4.8 pg; IL-6=7.1–7.3 pg; TNFα=25.1–26.3 pg; cAMP=0.4–0.6 nM; cGMP=0.85–0.95 nM; normal cGMP/cAMP=2.125; $\beta_2$-microglobulin=<1900 μg/l.

Example 5

A 28-year old white HIV$^+$/ARC male exhibiting waste syndrome, Herpes labialis and Herpes genitalis associated with widespread tissue damage, oral/pharyngeal candidiasis, polyarthralgias and tuberculosis was treated with defibrotide.

On Day 1 of treatment, a 360 mg/kg IV bolus of defibrotide was administered. Thereafter, a dose of 160–275 mg/kg/day was administered. Defibrotide was administered 86 days out of a 118 day treatment course.

Progressive increase in weight and amelioration of diarrhea was observed throughout the therapy period, a total weight gain of 12 kg occurring during the therapy period. Improvement in Karnofsky performance score started at day 3 and increased from a score of 3 to a score of 10 over the treatment period.

The effect on arthralgia was observed by the third consecutive day of treatment and was found to be strictly dose dependent. Upon cessation of therapy arthralgia relapsed to original condition and entered remission upon reinitiation of DNA therapy.

The effect on Herpes began on day 4 of treatment. By day 36 of the treatment period, genital Herpes lesions were in complete remission. By day 68, Herpes labialis lesions were in complete remission. No relapses were seen with temporary cessation of defibrotide.

Tables I and II summarize pertinent laboratory markers.

TABLE I

| TIME (days) | Absolute Lymphocyte | CD4 % | Absolute CD4 | CD8 % | Absolute CD8 | $B_2$-microglobulin |
|---|---|---|---|---|---|---|
| 1 | 1388 | 13.2 | 183 | 22 | 305 | N.D. |
| 26 | 1152 | 32.0 | 369 | 50 | 576 | N.D. |
| 90 | N.D. | N.D. | N.D. | N.D. | N.D. | 3582 |
| 104 | N.D. | N.D. | N.D. | N.D. | N.D. | 1348 |
| 118 | 3300 | 21.0 | 693 | 32 | 1056 | N.D. |

*N.D. = not determined

TABLE II

| TIME (days) | IL2 | TNFα | IL6 | cAMP | cGMP | cGMP/cAMP |
|---|---|---|---|---|---|---|
| 8 | 14.3 | 30.1 | 41.6 | 2.0 | 1.03 | 0.52 |
| 76 | 7.3 | 14.7 | 3.7 | 3.65 | 2.10 | 0.58 |

Elevated cAMP/cGMP was observed at the onset of therapy, signifying activation of both protein kinase A and protein kinase C pathways. A progressive rise in absolute and T lymphocyte numbers, CD4 and CD8 was seen. A decrease in IL1, IL-2, IL-6 and TNF-α was observed during treatment.

Complete remissions in accompanying disease states include Herpes labialis, oropharyngeal candidiasis, arthralgia, and Herpes genitalis as well as accompanying tissue damage. Complete normalization of TB findings (Chest x-ray) with apparent radiological remission occurred.

Example 6

A 25-year old white HIV$^+$ female was treated with defibrotide. At the onset of therapy, the patient was asymptomatic but had a low CD4 count.

On day 1 of the treatment, a 200 mg/kg IV bolus of defibrotide was administered. Thereafter a dose of 150–275 mg/kg/day was administered. Anabolic effects of the DNA were seen by day 13.

DNA therapy was terminated after 29 days secondary to a rise of CD4percent and absolute counts. DNA therapy was reinitiated 25 days later secondary to a decline in CD4 percent and absolute counts. Therapy was continued on an outpatient basis, intravenous administration being alternated with oral administration.

Tables III and IV summarize pertinent laboratory data. In this patient, all tested interleukin levels were normal.

TABLE III

| TIME (days) | Absolute Lymphocytes | CD4 % | Absolute CD4 | CD8 % | Absolute CD8 | $\beta_2$-microglobulin |
|---|---|---|---|---|---|---|
| TREATMENT CYCLE #1 | | | | | | |
| 1 | 973 | 15.2 | 148 | 20.1 | 196 | N.D. |
| 28 | 1100 | 48.0 | 528 | 50.0 | 550 | 3300 |
| TREATMENT CYCLE #2 | | | | | | |
| 1 | 429 | 34.0 | 146 | 22.0 | 94 | N.D. |
| 20 | 1945 | 15.0 | 292 | 20.0 | 389 | 2468 |
| 56 | 2600 | 29.0 | 754 | 20.0 | 520 | N.D. |

*N.D. = not determined

TABLE IV

| | TREATMENT CYCLE #2 | | |
|---|---|---|---|
| TIME (days) | cAMP | cGMP | cGMP/cAMP |
| 1 | 1.25 | 0.98 | 0.78 |
| 8 | 1.55 | 3.00 | 1.94 |
| 20 | 1.50 | 3.40 | 2.27 |

Treatment was characterized by increases in CD4, CD8, total lymphocyte, total T-lymphocyte counts accompanied by elevations in cAMP and cGMP, and in therapy related decreases in IL-6 and TNF-α. A total weight gain of 7 kg was observed.

Example 7

A 33-year old white male with AIDS and opportunistic infections including *Herpes labialis* associate with necrotic lesions, oral/pharyngeal candidiasis, tuberculosis and crytococcal diarrhea.

On day 1 of treatment, a 200 mg/kg IV bolus was administered. Treatment at a dose of 100–250 mg/kg/day was continued until day 40. The lower doses being given on days 7–13 having been reduced secondary to prolonged APTT. Treatment was thereafter discontinued due to unavailability of the drug. The patient died 8 days following cessation of therapy.

An anabolic effect was seen from day 6. Diarrhea was controlled from day 3 and cultures for cryptococcus became negative on day 15. Lesions of the lip began healing on day 5 and were completely healed by day 18. Odynophagia improved from day 5. Performance score began improving by day 3, reaching an optimum level of 5 between days 16 and 21.

Tables V and VI summarize pertinent laboratory data.

TABLE V

| TIME (days) | Absolute Lymphocytes | CD4% | Absolute CD4 | CD8% | Absolute CD8 |
|---|---|---|---|---|---|
| 7 | 700 | 10.0 | 70 | 29.0 | 203 |
| 18 | 800 | 10.0 | 80 | 17.0 | 136 |
| 44 | 700 | 8.0 | 56 | 14.0 | 98 |

TABLE VI

| TIME (days) | IL1 | IL2 | TNFα | IL6 | cAMP | cGMP | cGMP/cAMP |
|---|---|---|---|---|---|---|---|
| 21 | 105 | 18.0 | 95.1 | 40.6 | 1.4 | 1.1 | 0.79 |
| 33 | 85.5 | 7.6 | 14.8 | 45.1 | 1.5 | 0.96 | 0.64 |

Decline in elevated IL-1, IL-2 levels and complete normalization of TNF-α levels was observed. An increase in Il-6 was seen with cessation of therapy. At the time of death, a 3 kg weight gain was observed, and *Herpes labialis* and oral/pharyngeal candidiasis were in complete remission.

What is claimed is:

1. A method of treating a patient infected with HIV comprising administering intravenously defibrotide to the patient in an amount effective to cause disease markers associated with the HIV infection to return toward their status in an uninfected individual, wherein the dosage of defibrotide is between 40 mg/kg patient body weight to 400 mg/kg patient body weight per day.

2. A method of treating an HIV infection in a patient comprising the following steps:
 a) determining the initial state of a set of disease markers associated with the HIV infection, the disease markers being characteristics of the patient which deviate from an uninfected individual due to the HIV infection, wherein each disease marker in the set has a predetermined reference range indicative of an uninfected condition,
 b) administering intravenously to the patient a dose of defibrotide between 40 mg/kg patient body weight per day to 400 mg/kg patient body weight per day,
 c) screening a panel of second messengers and signal transducers, and selecting one or more of these as repair markers, where, as an indication of treatment efficacy, the concentration of the selected repair marker or repair markers deviates away from the concentration found in an uninfected individual following administration of defibrotide,
 d) administering defibrotide at a higher dose than the dose in b) and screening as in c),
 e) repeating step d) each time the concentration of the repair marker or repair markers selected in c) deviates further away from the concentration found in an uninfected individual following administration of a higher dose of defibrotide,
 f) repeating steps d) and e) until the concentration of the repair marker or repair markers selected in c) no longer deviates further away from the concentration found in an uninfected individual,
 g) continuing the administration of defibrotide at the highest dose in f) until the concentration of repair marker or repair markers selected in c) returns to the concentration found in an uninfected individual,
 h) administering defibrotide at a dosage higher than g) and repeating the steps of c), d), e), f) and g), screening for one or more additional repair markers until all disease markers determined in a) no longer deviate from that found in an uninfected individual.

3. The method of claim 2 further comprising:
 i) monitoring the repair marker or repair markers selected in steps c) and h) for three weeks following the last dose of defibrotide given in step h), wherein if the concern ration of one or more repair markers deviate from concentrations found in an uninfected individual, treatment is re-initiated in step g) at the highest dose given in step h).

4. A method of treating an HIV infection in a patient comprising the following steps:
 a) determining the initial state of a set of disease markers associated with an HIV infection, the disease markers being characteristics of the patient which deviate from an uninfected individual due to HIV infection, wherein each disease marker in the set has a predetermined reference range indicative of an uninfected condition,
 b) administering intravenously to the patient a dose of defibrotide between 40 mg/kg patient body weight per day to 400 mg/kg patient body weight per day,
 c) screening a panel of second messengers and signal transducers, and selecting one or more of these as repair markers, where, as an indication of treatment efficacy, the concentration of the selected repair marker or repair markers deviates away from the concentration found in an uninfected individual following administration of defibrotide, d) administering defibrotide at a higher dose than the dose in b) and screening as in c), e) repeating step d) each time the concentration of the repair marker or repair markers selected in c) deviates further away from the concentration found in an uninfected individual following administration of a higher dose of defibrotide, f) repeating steps d) and e) until the concentration of repair marker or repair markers selected in c) no longer deviates further away from the concentration found in an uninfected individual, g) continuing the administration of defibrotide at the highest dose in f) until the concentration of repair marker or repair markers selected in c) returns to the concentration found in an uninfected individual, h) administering defibrotide at a dosage higher than g) and repeating the steps of c), d), e), f) and g), screening for one or more additional repair markers until all disease markers determined in a) no longer deviate from that found in an uninfected individual, i) administering defibrotide at a dosage higher than h) and repeating the steps of c), d), e), f) and g), until the universal marker, vWAg, returns to the concentration found in an uninfected individual.

5. The method of claim 4 further comprising:

j) monitoring the concentration of vWAg for three weeks following the last dose of defibrotide given in step i), wherein if the concentration of vWAg deviates from the concentration found in an uninfected individual, treatment is re-initiated in step i) at the highest dose given in step i).

6. A method of treating an HIV infection in a patient comprising the following steps:

a) determining the initial state of a set of disease markers associated with the HIV infection, the disease markers being characteristics of the patient which deviate from an uninfected individual due to the HIV infection, wherein each disease marker in the set has a predetermined reference range indicative of an uninfected condition, b) administering intravenously to the patient a dose of defibrotide between 40 mg/kg patient body weight per day to 400 mg/kg patient body weight per day, wherein the concentration of vWAg increases to at least five times its concentration in an uninfected individual, and c) continuing to administer defibrotide within the dosage of step b) until the concentration of vWAg returns to the concentration found in an uninfected individual.

7. The method of claim 6 further comprising:

d) monitoring the concentration of vWAg for three weeks following the last dose of defibrotide given in step c), wherein if the concentration of vWAg deviates from the concentration found in an uninfected individual, treatment is re-initiated in step c) at the highest dose given in step c).

8. A method treating a patient infected with HIV, wherein HIV is not expressed, and wherein the patient has an elevation in the concentration of at least one immunological compound above the concentration of the compound in an uninfected individual comprising the following steps:

a) administering intravenously to the patient a dose of defibrotide between 40 mg/kg patient body weight per day to 400 mg/kg patient body weight per day, wherein the concentration of vWAg increases to at least five times its concentration in an uninfected individual, and b) continuing to administer defibrotide at the dosage of step a) until the concentration of vWAg returns to the concentration found in an uninfected individual.

9. The method of claim 8, wherein the immunological compound is selected from the group consisting of CD4, CD25, IL-1, IL-3, IL-4, 11-6, TNF and sIL2R.

10. The method of claims 1, 2, 4, 6, or 8 wherein the dose of defibrotide is from about 40 mg/kg patient body weight per day to about 350 mg/kg patient body weight per day and defibrotide is high molecular weight defibrotide.

11. The method of claims 1, 2, 4, 6, or 8 wherein the dose of defibrotide is from about 40 mg/kg patient body weight per day to about 600 mg/kg patient body weight per day and defibrotide is low molecular weight defibrotide.

12. The method of claims 2, 4, or 6 wherein said disease marker is selected from the group consisting of odynophagia, arthralgia, *Herpes labialis, Herpes genitalis*, cryptosporidium diarrhea, Karnofsky performance score, waste syndrome, oral and pharyngeal candidiasis, and tuberculosis.

13. The method of claim 2, 3, or 4 wherein said repair marker is selected from the group consisting of cAMP, cGMP, IL-1, IL-2, TNF-α, IL-6, cGMP/cAMP ratio, total lymphocyte count, T lymphocyte count, CD4 count, CD8 count, cAMP deA enzyme, adenn kinase A enzyme, adenylate cyclase, G-protein, phosphoinositol, protein kinase C enzyme, inositol triphosphate, diacylglycerol, intracellular calcium level, intracellular calcium ion level, c-myc, ms, c-fos, c-jun, NK-kB, EIAI, AP-1, COUP, TCF-1α, TATA, TAT element, oxygen radical, CREB, and CREM.

14. A method of treating a patient having an HIV associated disease state selected from the group consisting of tuberculosis or Herpesvirus infection comprising administering intravenously to the patient an amount of defibrotide of not less than about 40 mg/kg patient body weight per day to about 400 mg/kg body weight per day, wherein lesions caused by said infections go into remission.

15. A method of treating a patient having chronic wasting syndrome associated with HIV infection comprising administering intravenously to the patient an amount of defibrotide of not less than about 40 mg/kg patient body weight per day to about 400 mg/kg body weight per day, wherein the patient's Karnofsky performance score increases.

16. A method of stimulating tissue repair associated with HIV infection comprising administering intravenously to the patient an amount of defibrotide of not less than about 40 mg/kg patient body weight per day to about 400 mg/kg body weight per day, wherein tissue damage caused by said infection goes into remission.

17. A method of treating a patient having an HIV associated disease state selected from the group consisting of diarrhea, arthralgia and candidiasis comprising administering intravenously to the patient an amount of defibrotide of not less than about 40 mg/kg patient body weight per day to about 400 mg/kg body weight per day, wherein said disease state goes into remission.

* * * * *